(12) United States Patent
Kielszewski

(10) Patent No.: US 6,570,062 B1
(45) Date of Patent: May 27, 2003

(54) SYNTHETIC GENES FOR PLANT GUMS AND OTHER HYDROXYPROLINE-RICH GLYCOPROTEINS

(75) Inventor: Marcia J. Kielszewski, Albany, OH (US)

(73) Assignee: Ohio University, Athens, OH (US)

( * ) Notice: Subject to any disclaimer, the term of this patent is extended or adjusted under 35 U.S.C. 154(b) by 0 days.

(21) Appl. No.: 08/897,556

(22) Filed: Jul. 21, 1997

(51) Int. Cl.⁷ .................. C12N 15/29; C12N 15/82; C12P 19/04; C12P 21/02
(52) U.S. Cl. .............. 800/278; 800/284; 435/69.1; 435/70.1; 435/69.7; 435/69.8; 435/101; 435/320.1; 435/468; 435/419; 536/23.6
(58) Field of Search .................. 536/23.6, 23.1; 800/284, 278, 295, 298; 435/69.1, 468, 455, 471, 410, 418, 419, 320.1, 69.7, 70.1, 69.8, 101

(56) References Cited

U.S. PATENT DOCUMENTS

| | | | |
|---|---|---|---|
| 4,683,195 A | | 7/1987 | Mullis et al. .................. 435/6 |
| 4,683,202 A | | 7/1987 | Mullis .......................... 435/91 |
| 4,940,838 A | | 7/1990 | Schilperoort et al. ....... 800/205 |
| 4,965,188 A | | 10/1990 | Mullis et al. .................. 435/6 |
| 5,501,967 A | | 3/1996 | Offringa et al. ......... 435/172.3 |
| 5,584,807 A | | 12/1996 | McCabe ...................... 604/71 |
| 5,637,686 A | * | 6/1997 | Tjian et al. |
| 5,646,029 A | * | 7/1997 | Chen et al. .................. 435/325 |
| 5,695,971 A | | 12/1997 | Kadokami et al. |
| 5,728,810 A | | 3/1998 | Lewis et al. |
| 5,733,771 A | | 3/1998 | Lewis et al. |
| 5,756,677 A | | 5/1998 | Lewis et al. |
| 5,989,894 A | | 11/1999 | Lewis et al. |
| 5,994,099 A | | 11/1999 | Lewis et al. |
| 6,210,950 B1 | * | 4/2001 | Johnson et al. .......... 435/252.3 |

FOREIGN PATENT DOCUMENTS

WO    WO 92/20713    * 11/1992

OTHER PUBLICATIONS

Franssen . Accession No.: X69156. 1993.*
Sasaki et al. Accession No.: D41504. 1994.*
Woessner et al. Accession No.: S50755, 1994.*
Napoli et al. 1989. vol. 2: 278–289.*
Carvalho et al. The EMBO J. 1992. vol. 11: 2995–2602.*
Ishizuka et al. Accession No. AF 227194, Jan. 2000.*
Guilley et al. Virology 202(2):1012–1017, 1994.*
Woessner et al. Plant Mol. Biol. 26:947–960, 1994.*
Stiefel et al. Plant Mol. Biol. 11:483–493, 1988.*
de Blank et al. Plant Mol. Biol. 22(6):1167–1171, 1993.*
Memelink et al. Plant J. 4(6):1011–1022, 1993.*
Raz et al. Plant Mol. Biol. 16:365–367, 1991.*
Chiu et al. Curr. Biol. 6(3):325–330, 1996.*
Averyhart–Fullard et al. (1988) "A hydroxyproline–rich protein in the soybean cell wall," Proc Nat Acad Sci, USA 85:1082–1085.
Idris et al. (1998) "Characterisation of gum from *Acacia senegal* trees of different age and location using multidetection gel permeation chromatography," Food Hydrocolloids 12:379–388.
Islam et al. (1997) "A review of recent developments on the regulatory, structural and functional apsects of gum arabic," Food Hydrocolloids 11(4): 493–505.
Kieliszewski and Lamport (1986) "Cross–reactivities of polyclonal antibodies against extensin precursors determined via ELISA techniques," Phytochem. 25(3):673–677.
Kieliszewski et al (1992) "A repetitive proline–rich protein from the gymnosperm douglas fir is a hydroxyproline–rich glycoprotein," Plant Physiol. 98:919–926.
Kieliszewski and Lamport (1994) "Extensin: repetitive motifs, functional sites, post–translational codes, and phylogeny," The Plant J. 5(2):157–172.
Kieliszewski et al. (1995) "Tandem mass spectrometry and structural elucidation of glycopeptidases from a hydroxyproline–rich plant cell wall glycoprotein indicate that contiguous hydroxyproline residues are the major sites of hydroxyproline O–arabinosylation," J. Biol. Chemistry 270(6):2541–2549.
Kieliszewski et al. (1997) "Gum arabic glycoprotein: a new model," FASEB 11(9), Abstract #3286.
Lewis et al. (1996) "Expression and purification of a spider silk protein: a new strategy for producing repetitive proteins," Protein Expression and Purification 7:400–406.
Woessner et al. (1994) "Domain conservation in several volvocalean cell wall proteins," Plant Molec. Biol. 26:947–960.
Aspinall, "Plant Gums", *The Carbohydrates* 2B:522–536 (1970).
Anderson and McDougall, "The chemical characterization of the gum exudates from eight Australian Acacia species of the series Phyllodineae." *Food Hydrocolloids*, 2: 329–336 (1988).
Benfy et al., "Sequence Requirements of the 5–Enolpyruvylshikimate–3–phosphate Synthase 5'–Upstream Region for Tissue–Specific Expression in Flowers and Seedings," *Plant Cell*, 2:849–856 (1990).
Bidney et al., "Microprojectile bombardment of plant tissues increases transformation frequency by *Agrobacterium tumefaciens*," *Plant Molec. Biol.*, 18:301–313 (1992).
Colbere–Garapin F et al., "A New Dominant Hybird Selective Marker for Higher Eukaryotic Cells," *J. Mol. Biol.*, 150:1–14 (1981).

(List continued on next page.)

Primary Examiner—David T. Fox
(74) Attorney, Agent, or Firm—Medlen & Carroll, LLP

(57) ABSTRACT

A new approach in the field of plant gums is described which presents a new solution to the production of hydroxyproline (Hyp)-rich glycoproteins (HRGPs), repetitive proline-rich proteins (RPRPs) and arabino-galactan proteins (AGPs). The expression of synthetic genes designed from repetitive peptide sequences of such glycoproteins, including the peptide sequences of gum arabic glycoprotein (GAGP), is taught in host cells, including plant host cells.

19 Claims, 2 Drawing Sheets

OTHER PUBLICATIONS

Delonnay, "Determination of the Protein Constituent Of Gum Arabic" Master of Science Thesis (1993).

Dziezak, "A Focus on Gums," *Food Technology*, pp. 116–130 (Mar. 1991).

Fraley et al, "Liposome–mediated delivery of tobacco mosaic virus RNA into tobacco protoplasts: A sensitive assay for monitoring liposome–protoplast interactions," *Proc. Natl. Acad. Sci. USA*, 79:1859–1863 (1982).

Griesbach, "Incorporation of the gus gene into orchards via embryo electrophoresis," *HortScience*, 27:620 (1992).

Horsch et al., "A Simple and General Method for Transfeerring Genes into Plants," *Science*, 227:1229–1231 (1985).

Klee et al., "Agrobacterium–mediated plant transformation and its further applications to plant biology," *Ann. Rev. Plant Phys.*, 38:467–486 (1987).

Krens et al., "In vitro transformation of plant protoplasts with Ti–plasmid DNA," *Nature*, 296:72–74 (1982).

Lewis et al., *Protein Express. Purif.*, 7:400–406 (1996).

McGrath et al., "Chemical and Biosynthetic Approaches to the Production of Novel Polypeptide Materials," *Biotechnol. Prog.*, 6:188–192 (1990).

Mollard and J–P. Joseleau, "*Acacia senegal* cells cultured in suspension secrete a hydroxyproline–deficient rabinogalactan–protein," *Plant Physiol. Biochem.* 32:703–709 (1994).

Nan et al., "Genetic Transformation in Dendrobium (Orchid)," *In Biotechnology in Agriculture and Forestry*, Ed. Y.P.S. Bajaj, Springer–Verlag Berlin Heidelberg, 34:145–155 (1995).

Osman et al.,"Characteriztion of Gum Arabic Fractions Obtained By Anion–Exchange Chromatography," *Phytochemistry*, 38:409–417 (1984).

Prakash et al., "The effects of added proteins on the functionality of gum arbic in soft drink emulsion systems," *Food Hydrocolloids*, 4(3):177–184 (1990).

Qi et al.,"Gum Arabic Glycoprotin Is A Twisted Hairy Rope," *Plant Physiol.*, 96:848–855 (1991).

Rhodes CA et al., "Transformation of Maize by Electroporation of Embryos," *Methods Mol Biol*, 55:121–131 (1995).

Sambrook, J. et al., Molecular Cloning Laboratory Manual, 13.7–13.9 and 16.33–16.36 (1989) .

Stephen et al."Exudate Gums," *Methods Plant Biochem.*, 2:483–522 (1990).

Wigler M et al.,"Transformation of mammalian cells with an amplifiable dominant–acting gene," *Proc Natl Acad Sci* 77:3567–3570 (1980).

Zhang, X., Urry, D.W. and Daniell, H. "Expression of an environmentally friendly synthetic protein–based polymer gene in transgenic tobacco plants," *Plant Cell Reports*, 16: 174–179 (1996).

Kieliszewski, M.J. and Lamport, D.T.A., "Extensin: repetitive motifs, function sites, post–translational codes, and phylogeny" *The Plant Journal*, 5(2):157–172 (1994).

Averyhart–Fullard V., et al., "A hydroxyproline–rich protein in the soybean cell wall" *Proc Nat Acad Sci, USA*, 85:1082–1085 (1988).

* cited by examiner

```
     BamHI   XmaI
      |       |
GCT GGA TCC TCA ACC CGG GCC TCA CCA |CCA CCA CCT TCA CCT CCA CCC CCA TCT TCA|AGT GGT GGT GGA|S P P P P P P S S|CCA CCA CCT TCA CCT CCA CCC CCA TCT TCA|AGT GGA GGT GGT GGA|S P P P P P P P S|CCA CCA CCT TCA CCT CCA CCC CCA TCT TCA|AGT GGA GGT GGT GGA|S P P P P P P P S|CCA CCA CCT TCA CCT CCA|AGT GGT GGT GGA|S P P P P P|
CGA CCT AGG AGT TGG GCC CGG AGT GGT
 A   G   S   S   T   R   A   S   P

AgeI    EcoRI
                                                             |       |
                                                  TCA CCG GTC GCC CGG AAT TCA CCA CCC
                                                  AGT GGC CAG CGG GCC TTA AGT GGT GGG
                                                   S   P   V   A   R   N   S   P   P
```

FIG. 1

SYNTHETIC GENES FOR PLANT GUMS AND OTHER HYDROXYPROLINE-RICH GLYCOPROTEINS

FIELD OF THE INVENTION

The present invention relates generally to the field of plant gums and other hydroxyproline-rich glycoproteins, and in particular, to the expression of synthetic genes designed from repetitive peptide sequences.

BACKGROUND OF THE INVENTION

Gummosis is a common wound response that results in the exudation of a gum sealant at the site of cracks in bark. A. M. Stephen et. al.,"Exudate Gums", *Methods Plant Biochem.* (1990). Generally the exudate is a composite of polysaccharides and glycoproteins structurally related to cell wall components such as galactans [G. O. Aspinall, "Plant Gums", *The Carbohydrates* 2B:522536 (1970)] and hydroxyproline-rich glycoproteins [Anderson and McDougall, "The chemical characterization of the gum exudates from eight Australian Acacia species of the series Phyllodineae."*Food Hydrocolloids,* 2:329 (1988)].

Gum arabic is probably the best characterized of these exudates (although it has been largely refractory to chemical analysis). It is a natural plant exudate secreted by various species of Acacia trees. *Acacia senegal* accounts for approximately 80% of the production of gum arabic with *Acacia seyal, Acacia laeta, Acacia camplylacantha,* and *Acacia drepanolobium* supplying the remaining 20%. The gum is gathered by hand in Africa. It is a tedious process involving piercing and stripping the bark of the trees, then returning later to gather the dried tear drop shaped, spherical balls that form.

The exact chemical nature of gum arabic has not been elucidated. It is believed to consist of two major components, a microheterogeneous glucurono-arabinorhamnogalactan polysaccharide and a higher molecular weight hydroxyproline-rich glycoprotein. Osman et al.,"Characteriztion of Gum Arabic Fractions Obtained By Anion-Exchange Chromatography" Phytochemistry 38:409 (1984) and Qi et al.,"Gum Arabic Glycoprotein Is A Twisted Hairy Rope" Plant Physiol. 96:848 (1991). While the amino composition of the protein portion has been examined, little is known with regard to the precise amino acid sequence.

While the precise chemical nature of gum arabic is elusive, the gum is nonetheless particularly useful due to its high solubility and low viscosity compared to other gums. The FDA declared the gum to be a GRAS food additive. Consequently, it is widely used in the food industry as a thickener, emulsifier, stabilizer, surfactant, protective colloid, and flavor fixative or preservative. J. Dziezak, "A Focus on Gums" *Food Technology* (March 1991). It is also used extensively in the cosmetics industry.

Normally, the world production of gum arabic is over 100,000 tons per year. However, this production depends on the environmental and political stability of the region producing the gum. In the early 1970s, for example, a severe drought reduced gum production to 30,00 tons. Again in 1985, drought brought about shortages of the gum, resulting in a 600% price increase.

Three approaches have been used to deal with the somewhat precarious supply problem of gum arabic. First, other gums have been sought out in other regions of the world. Second, additives have been investigated to supplement inferior gum arabic. Third, production has been investigated in cultured cells.

The effort to find other gums in other regions of the world has met with some limited success. However, the solubility of gum arabic from Acacia is superior to other gums because it dissolves well in either hot or cold water. Moreover, while other exudates are limited to a 5% solution because of their excessive viscosity, gum arabic can be dissolved readily to make 55% solutions.

Some additives have been identified to supplement gum arabic. For example, whey proteins can be used to increase the functionality of gum arabic. A. Prakash et al., "The effects of added proteins on the functionality of gum arabic in soft drink emulsion systems," *Food Hydrocolloids* 4:177 (1990). However, this approach has limitations. Only low concentrations of such additives can be used without producing off-flavors in the final food product.

Attempts to produce gum arabic in cultured *Acacia Senegal* cells has been explored. Unfortunately, conditions have not been found which lead to the expression of gum arabic in culture. A. Mollard and J-P. Joseleau, "*Acacia Senegal* cells cultured in suspension secrete a hydroxyproline-deficient rabinogalactan-protein" Plant Physiol. Biochem. 32:703 (1994).

Clearly, new approaches to improve gum arabic production are needed. Such approaches should not be dependent on environmental or political factors. Ideally, such approaches should simplify production and be relatively inexpensive.

SUMMARY OF THE INVENTION

The present invention involves a new approach in the field of plant gums and presents a new solution to the production of hydroxyproline(Hyp)-rich glycoproteins (HRGPs), repetitive proline-rich proteins (RPRPs) and arabinogalactan proteins (AGPs). The present invention contemplates the expression of synthetic genes designed from repetitive peptide sequences of such glycoproteins, including the peptide sequences of gum arabic glycoprotein (GAGP).

With respect to GAGP, the present invention contemplates a substantially purified polypeptide comprising at least a portion of the amino acid sequence Ser-Hyp-Hyp-Hyp-[Hyp/Thr]-Leu-Ser-Hyp-Ser-Hyp-Thr-Hyp-Thr-Hyp-Hyp-Hyp-Gly-Pro-His (SEQ ID NO:1 and SEQ ID NO:2) or variants thereof. By "variants" it is meant that the sequence need not comprise the exact sequence; up to five (5) amino acid substitutions are contemplated. For example, a Leu or Hyp may be substituted for the Gly; Leu may also be substituted for Ser and one or more Hyp. By "variants" it is also meant that the sequence need not be the entire nineteen (19) amino acids. Illustrative variants are shown in Table 2.

Indeed, it is not intended that the present invention be limited by the precise length of the purified polypeptide. In one embodiment, the peptide comprises more than twelve (12) amino acids from the nineteen (19) amino acids of the sequence. In another embodiment, a portion of the nineteen (19) amino acids (see SEQ ID NO:1 and SEQ ID NO:2) is utilized as a repetitive sequence. In yet another embodiment, all nineteen (19) amino acids (see SEQ ID NO:1 and SEQ ID NO:2) with or without amino acid substitutions) are utilized as a repetitive sequence.

It is not intended that the present invention be limited by the precise number of repeats. The sequence (i.e. SEQ ID NO:1 and SEQ ID NO:2) or variants thereof may be used as a repeating sequence between one (1) and up to fifty (50)

times, more preferably between ten (10) and up to thirty (30) times, and most preferably approximately twenty (20) times. The sequence (i.e. SEQ ID NO:1 and SEQ ID NO:2) or variants thereof may be used as contiguous repeats or may be used as non-contiguous repeats (with other amino acids, or amino acid analogues, placed between the repeating sequences).

The present invention specifically contemplates fusion proteins comprising a non-gum arabic protein or glycoprotein sequence and a portion of the gum arabic glycoprotein sequence (SEQ ID NO:1 and SEQ ID NO:2). It is not intended that the present invention be limited by the nature of the non-gum arabic glycoprotein sequence. In one embodiment, the non-gum arabic glycoprotein sequence is a green fluorescent protein.

As noted above, the present invention contemplates synthetic genes encoding such peptides. By "synthetic genes" it is meant that the nucleic acid sequence is derived using the peptide sequence of interest (in contrast to using the nucleic acid sequence from cDNA). In one embodiment, the present invention contemplates an isolated polynucleotide sequence encoding a polypeptide comprising at least a portion of the polypeptide of SEQ ID NO:1 and SEQ ID NO:2 or variants thereof. The present invention specifically contemplates a polynucleotide sequence comprising a nucleotide sequence encoding a polypeptide comprising one or more repeats of SEQ ID NO:1 and SEQ ID NO:2 or variants thereof. Importantly, it is not intended that the present invention be limited to the precise nucleic acid sequence encoding the polypeptide of interest.

The present invention contemplates synthetic genes encoding portions of HRGPs, wherein the encoded peptides contain one or more of the highly conserved Ser-Hyp$_4$ (SEQ ID NO:3) motif(s). The present invention also contemplates synthetic genes encoding portions of RPRPs, wherein the encoded peptides contain one or more of the pentapeptide motif: Pro-Hyp-Val-Tyr-Lys (SEQ ID NO:4) and variants of this sequence such as X-Hyp-Val-Tyr-Lys (SEQ ID NO:5) and Pro-Hyp-Val-X-Lys (SEQ ID NO:6) and Pro-Pro-X-Tyr-Lys and Pro-Pro-X-Tyr-X (SEQ ID NO:8), where "X" can be Thr, Glu, Hyp, Pro, His and Ile. The present invention also contemplates synthetic genes encoding portions of AGPs, wherein the encoded peptides contain one or more Xaa-Hyp-Xaa-Hyp (SEQ ID NO:9) repeats. Such peptides can be expressed in a variety of forms, including but not limited to fusion proteins.

With regard to motifs for HRGPs, the present invention contemplates a polynucleotide sequence comprising the sequence: 5'-CCA CCA CCT TCA CCT CCA CCC CCA TCT CCA-3' (SEQ ID NO:10). With regard to motifs for AGPs, the present invention contemplates a polynucleotide sequence comprising the sequence: 5'-TCA CCA TCA CCA TCT CCT TCG CCA TCA CCC-3' (SEQ ID NO:11). Of course, it is not intended that the present invention be limited by the particular sequence. Indeed, the present invention specifically contemplates sequences homologous to the sequences of SEQ ID NOS: 10 and 11. The present invention also contemplates sequences that are complementary (including sequences that are only partially complementary) sequences to the sequences of SEQ ID NOS: 10 and 11. Such complementary sequences include sequences that will hybridize to the sequences of SEQ ID NOS: 10 and 11 under low stringency conditions as well as high stringency conditions (see Definitions below).

The present invention also contemplates the mixing of motifs (i.e. modules) which are not found in wild-type sequences. For example, one might add GAGP modules to extensin and RPRP crosslinking modules to AGP-like molecules.

The present invention contemplates using the polynucleotides of the present invention for expression of the polypeptides in vitro and in vivo. Therefore, the present invention contemplates polynucleotide sequences encoding two or more repeats of the sequence of SEQ ID NO:1 and SEQ ID NO:2 or variants thereof, wherein said polynucleotide sequence is contained on a recombinant expression vector. It is also contemplated that such vectors will be introduced into a variety of host cells, both eukaryotic and prokaryotic (e.g. bacteria such as *E. coli*).

In one embodiment, the vector further comprises a promoter. It is not intended that the present invention be limited to a particular promoter. Any promoter sequence which is capable of directing expression of an operably linked nucleic acid sequence encoding a portion of a plant gum polypeptide (or other hydroxyproline-rich polypeptide of interest as described above) is contemplated to be within the scope of the invention. Promoters include, but are not limited to, promoter sequences of bacterial, viral and plant origins. Promoters of bacterial origin include, but are not limited to, the octopine synthase promoter, the nopaline synthase promoter and other promoters derived from native Ti plasmids. Viral promoters include, but are not limited to, the 35S and 19S RNA promoters of cauliflower mosaic virus (CaMV), and T-DNA promoters from Agrobacterium. Plant promoters include, but are not limited to, the ribulose-1,3-bisphosphate carboxylase small subunit promoter, maize ubiquitin promoters, the phaseolin promoter, the E8 promoter, and the Tob7 promoter.

The invention is not limited to the number of promoters used to control expression of a nucleic acid sequence of interest. Any number of promoters may be used so long as expression of the nucleic acid sequence of interest is controlled in a desired manner. Furthermore, the selection of a promoter may be governed by the desirability that expression be over the whole plant, or localized to selected tissues of the plant, e.g., root, leaves, fruit, etc. For example, promoters active in flowers are known (Benfy et al. (1990) Plant Cell 2:849–856).

The promoter activity of any nucleic acid sequence in host cells may be determined (i.e., measured or assessed) using methods well known in the art and exemplified herein. For example, a candidate promoter sequence may be tested by ligating it in-frame to a reporter gene sequence to generate a reporter construct, introducing the reporter construct into host cells (e.g. tomato or potato cells) using methods described herein, and detecting the expression of the reporter gene (e.g., detecting the presence of encoded mRNA or encoded protein, or the activity of a protein encoded by the reporter gene). The reporter gene may confer antibiotic or herbicide resistance. Examples of reporter genes include, but are not limited to, dhfr which confers resistance to methotrexate [Wigler M et al., (1980) *Proc Natl Acad Sci* 77:3567–70]; npt, which confers resistance to the aminoglycosides neomycin and G-418 [Colbere-Garapin F et al., (1981) *J. Mol. Biol.* 150:1–14] and als or pat, which confer resistance to chlorsulfuron and phosphinotricin acetyl transferase, respectively. Recently, the use of a reporter gene system which expresses visible markers has gained popularity with such markers as β-glucuronidase and its substrate (X-Gluc), luciferase and its substrate (luciferin), and β-galactosidase and its substrate (X-Gal) being widely used not only to identify transformants, but also to quantify the amount of transient or stable protein expression attributable to a specific vector system [Rhodes C A et al. (1995) Methods Mol Biol 55:121–131].

In addition to a promoter sequence, the expression construct preferably contains a transcription termination sequence downstream of the nucleic acid sequence of interest to provide for efficient termination. In one embodiment, the termination sequence is the nopaline synthase (NOS) sequence. In another embodiment the termination region comprises different fragments of sugarcane ribulose-1,5-biphosphate carboxylase/oxygenase (rubisco) small subunit (scrbcs) gene. The termination sequences of the expression constructs are not critical to the invention. The termination sequence may be obtained from the same gene as the promoter sequence or may be obtained form different genes.

If the mRNA encoded by the nucleic acid sequence of interest is to be efficiently translated, polyadenylation sequences are also commonly added to the expression construct. Examples of the polyadenylation sequences include, but are not limited to, the Agrobacterium octopine synthase signal, or the nopaline synthase signal.

The invention is not limited to constructs which express a single nucleic acid sequence of interest. Constructs which contain a plurality of (i.e., two or more) nucleic acid sequences under the transcriptional control of the same promoter sequence are expressly contemplated to be within the scope of the invention. Also included within the scope of this invention are constructs which contain the same or different nucleic acid sequences under the transcriptional control of different promoters. Such constructs may be desirable to, for example, target expression of the same or different nucleic acid sequences of interest to selected plant tissues.

As noted above, the present invention contemplates using the polynucleotides of the present invention for expression of a portion of plant gum polypeptides in vitro and in vivo. Where expression takes place in vivo, the present invention contemplates transgenic plants. The transgenic plants of the invention are not limited to plants in which each and every cell expresses the nucleic acid sequence of interest. Included within the scope of this invention is any plant (e.g. tobacco, tomato, maize, algae, etc.) which contains at least one cell which expresses the nucleic acid sequence of interest. It is preferred, though not necessary, that the transgenic plant express the nucleic acid sequence of interest in more than one cell, and more preferably in one or more tissue. It is particularly preferred that expression be followed by proper glycosylation of the plant gum polypeptide fragment or variant thereof, such that the host cell produces functional (e.g. in terms of use in the food or cosmetic industry) plant gum polypeptide.

The fact that transformation of plant cells has taken place with the nucleic acid sequence of interest may be determined using any number of methods known in the art. Such methods include, but are not limited to, restriction mapping of genomic DNA, PCR analysis, DNA-DNA hybridization, DNA-RNA hybridization, and DNA sequence analysis.

Expressed polypeptides (or fragments thereof) can be immobilized (covalently or non-covalently) on solid supports or resins for use in isolating HRGP-binding molecules from a variety of sources (e.g. algae, plants, animals, microorganisms). Such polypeptides can also be used to make antibodies.

DESCRIPTION OF THE DRAWINGS

FIG. 1 shows the nucleic acid sequence (SEQ ID NO:12) of one embodiment of a synthetic gene of the present invention.

DEFINITIONS

Figure 2:
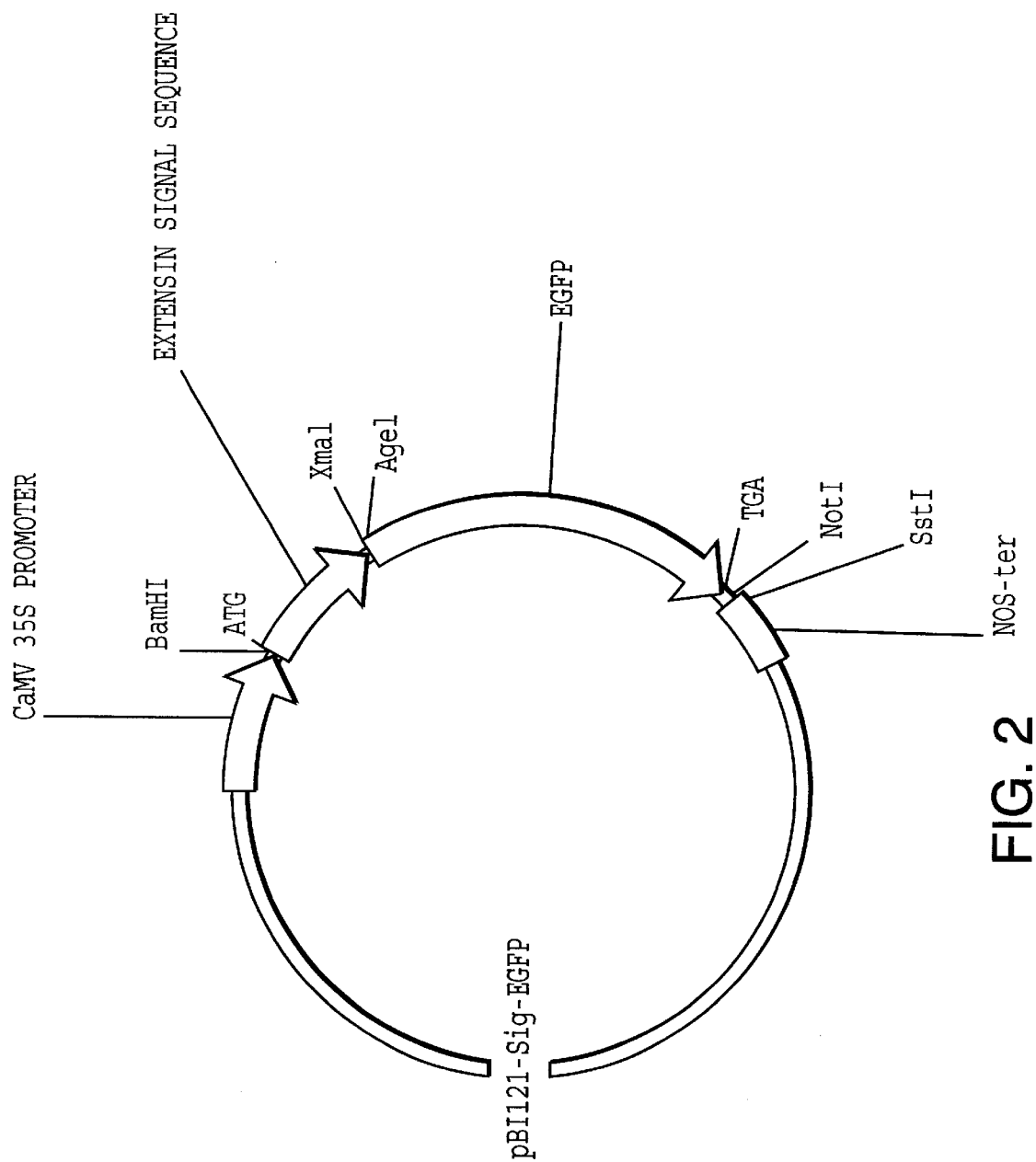
FIG. 2 shows one embodiment of a synthetic gene in one embodiment of an expression vector.

The term "gene" refers to a DNA sequence that comprises control and coding sequences necessary for the production of a polypeptide or its precursor. The polypeptide can be encoded by a full length coding sequence or by any portion of the coding sequence.

The term "nucleic acid sequence of interest" refers to any nucleic acid sequence the manipulation of which may be deemed desirable for any reason by one of ordinary skill in the art (e.g., confer improved qualities).

The term "wild-type" when made in reference to a gene refers to a gene which has the characteristics of a gene isolated from a naturally occurring source. The term "wild-type" when made in reference to a gene product refers to a gene product which has the characteristics of a gene product isolated from a naturally occurring source. A wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "recombinant" when made in reference to a DNA molecule refers to a DNA molecule which is comprised of segments of DNA joined together by means of molecular biological techniques. The term "recombinant" when made in reference to a protein or a polypeptide refers to a protein molecule which is expressed using a recombinant DNA molecule.

As used herein, the terms "vector" and "vehicle" are used interchangeably in reference to nucleic acid molecules that transfer DNA segment(s) from one cell to another.

The term "expression vector" or "expression cassette" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "targeting vector" or "targeting construct" refer to oligonucleotide sequences comprising a gene of interest flanked on either side by a recognition sequence which is capable of homologous recombination of the DNA sequence located between the flanking recognition sequences.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "transformation" as used herein refers to the introduction of foreign DNA into cells. Transformation of a plant cell may be accomplished by a variety of means known in the art including particle mediated gene transfer (see, e.g., U.S. Pat. No. 5,584,807 hereby incorporated by reference); infection with an Agrobacterium strain containing the foreign DNA for random integration (U.S. Pat. No. 4,940,838 hereby incorporated by reference) or targeted integration (U.S. Pat. No. 5,501,967 hereby incorporated by reference) of the foreign DNA into the plant cell genome;

electroinjection (Nan et al. (1995) In "Biotechnology in Agriculture and Forestry," Ed. Y. P. S. Bajaj, Springer-Verlag Berlin Heidelberg, Vol 34:145–155; Griesbach (1992) HortScience 27:620); fusion with liposomes, lysosomes, cells, minicells or other fusible lipid-surfaced bodies (Fraley et al. (1982) *Proc. Natl. Acad. Sci. USA* 79:1859–1863; polyethylene glycol (Krens et al. (1982) *Nature* 296:72–74); chemicals that increase free DNA uptake; transformation using virus, and the like.

The terms "infecting" and "infection" with a bacterium refer to co-incubation of a target biological sample, (e.g., cell, tissue, etc.) with the bacterium under conditions such that nucleic acid sequences contained within the bacterium are introduced into one or more cells of the target biological sample.

The term "Agrobacterium" refers to a soil-borne, Gram-negative, rod-shaped phytopathogenic bacterium which causes crown gall. The term "Agrobacterium" includes, but is not limited to, the strains *Agrobacterium tumefaciens*, (which typically causes crown gall in infected plants), and *Agrobacterium rhizogens* (which causes hairy root disease in infected host plants). Infection of a plant cell with Agrobacterium generally results in the production of opines (e.g., nopaline, agropine, octopine etc.) by the infected cell. Thus, Agrobacterium strains which cause production of nopaline (e.g., strain LBA4301, C58, A208) are referred to as "nopaline-type" Agrobacteria; Agrobacterium strains which cause production of octopine (e.g., strain LBA4404, Ach5, B6) are referred to as "octopine-type" Agrobacteria; and Agrobacterium strains which cause production of agropine (e.g., strain EHA105, EHA101, A281) are referred to as "agropine-type" Agrobacteria.

The terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are herein incorporated by reference), and are commercially available (e.g., the helium gas-driven microprojectile accelerator (PDS-1000/He) (BioRad).

The term "microwounding" when made in reference to plant tissue refers to the introduction of microscopic wounds in that tissue. Microwounding may be achieved by, for example, particle or biolistic bombardment.

The term "transgenic" when used in reference to a plant cell refers to a plant cell which comprises a transgene, or whose genome has been altered by the introduction of a transgene. The term "transgenic" when used in reference to a plant refers to a plant which comprises one or more cells which contain a transgene, or whose genome has been altered by the introduction of a transgene. These transgenic cells and transgenic plants may be produced by several methods including the introduction of a "transgene" comprising nucleic acid (usually DNA) into a target cell or integration into a chromosome of a target cell by way of human intervention, such as by the methods described herein.

The term "transgene" as used herein refers to any nucleic acid sequence which is introduced into the genome of a plant cell by experimental manipulations. A transgene may be an "endogenous DNA sequence," or a "heterologous DNA sequence" (i.e., "foreign DNA"). The term "endogenous DNA sequence" refers to a nucleotide sequence which is naturally found in the cell into which it is introduced so long as it does not contain some modification (e.g., a point mutation, the presence of a selectable marker gene, etc.) relative to the naturally-occurring sequence. The term "heterologous DNA sequence" refers to a nucleotide sequence which is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes an endogenous DNA sequence which contains some modification. Generally, although not necessarily, heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

As used herein, the term "probe" when made in reference to an oligonucleotide (i.e., a sequence of nucleotides) refers to an oligonucleotide, whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. Oligonucleotide probes may be labelled with a "reporter molecule," so that the probe is detectable using a detection system. Detection systems include, but are not limited to, enzyme, fluorescent, radioactive, and luminescent systems.

The term "selectable marker" as used herein, refer to a gene which encodes an enzyme having an activity that confers resistance to an antibiotic or drug upon the cell in which the selectable marker is expressed. Selectable markers may be "positive" or "negative." Examples of positive selectable markers include the neomycin phosphotrasferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mNRA.

The term "amplification" is defined as the production of additional copies of a nucleic acid sequence and is generally carried out using polymerase chain reaction technologies well known in the art [Dieffenbach C W and G S Dveksler (1995) PCR *Primer, a Laboratory Manual,* Cold Spring Harbor Press, Plainview N.Y.]. As used herein, the term "polymerase chain reaction" ("PCR") refers to the method of K. B. Mullis disclosed in U.S. Pat. Nos. 4,683,195, 4,683,202 and 4,965,188, all of which are hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; and/or incorporation of $^{32}$P-labeled deoxyribonucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences may be used to obtain segments of DNA (e.g., genes) for the construction of targeting vectors, transgenes, etc.

The present invention contemplates using amplification techniques such as PCR to obtain the cDNA (or portions thereof) of plant genes encoding plant gums and other hydroxyproline-rich polypeptides. In one embodiment, primers are designed using the synthetic gene sequences (e.g. containing sequences encoding particular motifs) described herein and PCR is carried out (using genomic DNA or other source of nucleic acid from any plant capable of producing a gum exudate) under conditions of low stringency. In another embodiment, PCR is carried out under high stringency. The amplified products can be run out on a gel and isolated from the gel.

The term "hybridization" as used herein refers to any process by which a strand of nucleic acid joins with a complementary strand through base pairing [Coombs J (1994) *Dictionary of Biotechnology,* Stockton Press, New York N.Y.].

As used herein, the terms "complementary" or "complementarity" when used in reference to polynucleotides refer to polynucleotides which are related by the base-pairing rules. For example, for the sequence 5'-AGT-3' is complementary to the sequence 5'-ACT-3'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions,.as well as detection methods which depend upon binding between nucleic acids.

The term "homology" when used in relation to nucleic acids refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

Low stringency conditions when used in reference to nucleic acid hybridization comprise conditions equivalent to binding or hybridization at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SODS at 42° C. when a probe of about 500 nucleotides in length is employed.

High stringency conditions when used in reference to nucleic acid hybridization comprise conditions equivalent to binding or hybridization at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.5% SODS, 5×Denhardt's reagent and 100 µg/ml denatured salmon sperm DNA followed by washing in a solution comprising 0.1×SSPE, 1.0% SODS at 42° C. when a probe of about 500 nucleotides in length is employed.

When used in reference to nucleic acid hybridization the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions.

"Stringency" when used in reference to nucleic acid hybridization typically occurs in a range from about $T_m$–5° C. (5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences. Under "stringent conditions" a nucleic acid sequence of interest will hybridize to its exact complement and closely related sequences.

As used herein, the term "fusion protein" refers to a chimeric protein containing the protein of interest (i.e., GAGP and fragments thereof) joined to an exogenous protein fragment (the fusion partner which consists of a non-GAGP sequence). The fusion partner may provide a detectable moiety, may provide an affinity tag to allow purification of the recombinant fusion protein from the host cell, or both. If desired, the fusion protein may be removed from the protein of interest (i.e., GAGP protein or fragments thereof) by a variety of enzymatic or chemical means known to the art.

As used herein the term "non-gum arabic glycoprotein" or "non-gum arabic glycoprotein sequence" refers to that portion of a fusion protein which comprises a protein or protein sequence which is not derived from a gum arabic glycoprotein.

The term "protein of interest" as used herein refers to the protein whose expression is desired within the fusion protein. In a fusion protein the protein of interest (e.g., GAGP) will be joined or fused with another protein or protein domain (e.g., GFP), the fusion partner, to allow for enhanced stability of the protein of interest and/or ease of purification of the fusion protein.

As used herein, the term "purified" or "to purify" refers to the removal of contaminants from a sample. For example, recombinant HRGP polypeptides, including HRGP-GFP fusion proteins are purified by the removal of host cell components such as nucleic acids, lipopolysaccharide (e.g., endotoxin).

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed from a recombinant DNA molecule.

As used herein the term "portion" when in reference to a protein (as in "a portion of a given protein") refers to fragments of that protein. The fragments may range in size from four amino acid residues to the entire amino acid sequence minus one amino acid.

DETAILED DESCRIPTION OF INVENTION

A The present invention relates generally to the field of plant gums and other hydroxyproline-rich glycoproteins, and in particular, to the expression of synthetic genes designed from repetitive peptide sequences. The hydroxyproline-rich glycoprotein (HRGP) superfamily is ubiquitous in the primary cell wall or extracellular matrix throughout the plant kingdom. Family members are diverse in structure and implicated in all aspects of plant growth and development. This includes plant responses to stress imposed by pathogenesis and mechanical wounding.

Plant HRGPs have no known animal homologues. Furthermore, hydroxyproline residues are O-glycosylated in plant glycoproteins but never in animals. At the molecular level the function of these unique plant glycoproteins remains largely unexplored.

HRGPS are, to a lesser or greater extent, extended, repetitive, modular proteins. The modules are small (generally 4–6 residue motifs), usually glycosylated, with most HRGPs being made up of more than one type of repetitive module. For purposes of constructing the synthetic genes of the present invention, it is useful to view the glycosylated polypeptide modules not merely as peptides or oligosaccharides but as small functional units.

The description of the invention involves A) the design of the polypeptide of interest, B) the production of synthetic genes encoding the polypeptide of interest, C) the construction of the expression vectors, D) selection of the host cells, and E) introduction of the expression construct into a particular cell (whether in vitro or in vivo).

A. Design of the Polypeptide of Interest

The present invention contemplates polypeptides that are fragments of hydroxyproline-rich glycoproteins (HRGPs), repetitive proline-rich proteins (RPRPs) and arabinogalactan proteins (AGPs). The present invention contemplates portions of HRGPs comprising one or more of the highly conserved Ser-Hyp$_4$ (SEQ ID NO:3) motif(s). The present invention also contemplates portions of RPRPs comprising one or more of the pentapeptide motif: Pro-Hyp-Val-Tyr-Lys (SEQ ID NO:4). The present invention also contemplates portions of AGPs comprising one or more Xaa-Hyp-Xaa-Hyp (SEQ ID NO:9) repeats.

While an understanding of the natural mechanism of glycosylation is not required for the successful operation of the present invention, it is believed that in GAGP and other HRGPs, repetitive Xaa-Hyp blocks constitute a Hyp-glycosylation code where Hyp occurring in contiguous blocks (Xaa-Hyp-Hyp) and Hyp occurring in non-contiguous Hyp repeats is recognized by different enzymes: arabinosyltransferases and galactosyltransferases, respectively.

The RPRPs (and some nodulins) consist of short repetitive blocks (e.g. Soybean RPRPI: [POVYK]$_n$ where O=Hyp) containing the least amount of contiguous Hyp. They also exemplify the low end of the glycosylation range with relatively few Hyp residues arabinosylated and no arabinogalactan polysaccharide. For example, in soybean RPRP1, L-arabinofuranose is attached to perhaps only a single Hyp residue in the molecule.

The Extensins occupy an intermediate position in the glycosylation continuum, containing about 50% carbohydrate which occurs mainly as Hyp-arabinosides (1–4 Ara residues), but not as Hyp-arabinogalactan polysaccharide. Extensins contain the repetitive, highly arabinosylated, diagnostic Ser-Hyp$_4$ (SEQ ID NO:3) glycopeptide module. The precise function of this module is unknown, but earlier work indicates that these blocks of arabinosylated Hyp help stabilize the extended polyproline-II helix of the extensins. Monogalactose also occurs on the Ser residues.

The classical Ser-Hyp$_4$ (SEQ ID NO:3) glycopeptide module is of special interest. A tetra-L-arabinofuranosyl oligosaccharide is attached to each Hyp residue in the block. Three uniquely b-linked arabinofuranosyl residues and an a-linked nonreducing terminus comprise the tetraarabinoo-ligosaccharide. While an understanding of the natural mechanism of glycosylation is not required for the successful operation of the present invention, it is believed that the arabinosylated Hyp residues together with the single galactosyl-serine residue undoubtedly form a unique molecular surface topography which interacts with and is recognized by other wall components, possibly including itself. Shorter blocks of Hyp, namely $Hyp_3$ and $Hyp_2$, lack the fourth (a-linked) arabinose residue, again suggesting that the fourth Ara unique to the $Hyp_4$ block, has a special role and is presented for recognition or cleavage.

At the high end of the glycosylation range (~90% sugar), the arabinogalactan-proteins (AGPs) and the related gum arabic glycoprotein (GAGP) are uniquely glycosylated with arabinogalactan polysaccharides. GAGP and all AGPs so far characterized by Hyp-glycoside profiles contain Hyp-linked arabinosides assigned to contiguous Hyp residues by the Hyp contiguity hypothesis. However these glycoproteins also uniquely contain (Xaa-Hyp-Xaa-Hyp (SEQ ID NO:9)) repeats. These repeats are putative polysaccharide attachment sites.

The present invention contemplates in particular fragments of gum arabic glycoprotein (GAGP). As noted above, GAGP has been largely refractory to chemical analysis. The largest peptide obtained and sequenced from gum arabic was a peptide of twelve (12) amino acids having the sequence Ser-Hyp-Ser-Hyp-Thr-Hyp-Thr-Hyp-Hyp-Hyp-Gly-Pro (SEQ ID NO:13). C. L. Delonnay, "Determination of the Protein Constituent Of Gum Arabic" Master of Science Thesis (1993). The present invention contemplates using this Delonnay sequence as well as (heretofore undescribed) larger peptide fragments of GAGP (and variants thereof) for the design of synthetic genes. In this manner, "designer plant gums" can be produced ("designer extensins" are also contemplated).

In one embodiment, the present invention contemplates a substantially purified polypeptide comprising at least a portion of the amino acid consensus sequence Ser-Hyp-Hyp-Hyp-[Hyp/Thr]-Leu-Ser-Hyp-Ser-Hyp-Thr-Hyp-Thr-Hyp-Hyp-Hyp-Gly-Pro-His (SEQ ID NO:1 and SEQ ID NO:2) or variants thereof. While an understanding of the natural mechanism of glycosylation is not required for the successful operation of the present invention, it is believed that this GAGP 19-residue consensus repeat (which contains both contiguous Hyp and non-contiguous Hyp repeats) is glycosylated in native GAGP with both Hyp-arabinosides and Hyp-polysaccharide in molar ratios. It is further believed that the high molecular weight protein component of gum arabic (i.e. GAGP) is responsible for the remarkable emulsifying and stabilizing activity exploited by the food and soft drink industries.

B. Production of Synthetic Genes

The present invention contemplates the use of synthetic genes engineered for the expression of repetitive glycopeptide modules in cells, including but not limited to callus and suspension cultures. It is not intended that the present invention be limited by the precise number of repeats.

In one embodiment, the present invention contemplates the nucleic acid sequences encoding the consensus sequence for GAGP (i.e. SEQ ID NO: 1 and SEQ ID NO:2) or variants thereof may be used as a repeating sequence between two (2) and up to fifty (50) times, more preferably between ten (10) and up to thirty (30) times, and most preferably approximately twenty (20) times. The nucleic acid sequence encoding the consensus sequence (i.e. SEQ ID NO:1 and SEQ ID NO:2) or variants thereof may be used as contiguous repeats or may be used as non-contiguous repeats.

In designing any HRGP gene cassette the following guidelines are employed. Cassette design reflects the following:

1) Minimization of the repetitive nature of the coding sequence while still taking into account the HRGP codon bias of the host plant (e.g., when tomato is the host plant, the codon usage bias of the tomato which favors CCA and CCT [but not CCG] for Pro residues, and TCA and TCC for Ser residues is employed). *Zea mays* (such as corn) and perhaps other graminaceous monocots (e.g. rice barley, wheat and all grasses) prefer CCG and CCC for proline; GTC and CTT for valine,; and AAG for lysine. Dicots (including legumes) prefer CCA and CCT for proline and TCA and TCT for serine.

2) Minimization of strict sequence periodicity.

3) Non-palindromic ends are used for the monomers and end linkers to assure proper "head-to-tail" polymerization.

4) The constructs contain no internal restriction enzyme recognition sites for the restriction enzymes employed for the insertion of these sequences into expression vectors or during subsequent manipulations of such vectors. Typically, the 5' linker contains a XmaI site downstream of the BamHI site used for cloning into the cloning vector (e.g., pBluescript). The XmaI site is used for insertion of the HRGP gene cassette into the expression vector (e.g., pBI121-Sig-EGFP). Typically, the 3' linker contains a AgeI site upstream of the EcoRI site used for cloning into the cloning vector (e.g., pBluescript). The AgeI site is used for insertion of the HRGP gene cassette into the expression vector. (For plasmid pBI121-Sig—which does not contain GFP for the fusion protein—the same signal sequence is used, but the 3' linkers contain an Sst I restriction site for insertion as an Xma I/Sst I fragment behind the signal sequence and before the NOS terminator.

5) The oligonucleotides used are high quality (e.g., from GibcoBRL, Operon) and have been purified away from unwanted products of the synthesis.

6) The $T_M$ of correctly aligned oligomers is greater than the $T_M$ of possible dimers, hairpins or crossdimers.

C. Construction of Expression Vectors

It is not intended that the present invention be limited by the nature of the expression vector. A variety of vectors are contemplated. In one embodiment, two plant transformation vectors are prepared, both derived from pBI121 (Clontech). Both contain an extensin signal sequence for transport of the constructs through the ER/Golgi for posttranslational modification. A first plasmid construct containd Green Fluorescent Protein (GFP) as a reporter protein instead of GUS. A second plasmid does not contain GFP.

pBI121 is the Jefferson vector in which the BamHI and SstI sites can be used to insert foreign DNA between the 35S CaMV promoter and the termination/polyadenylation signal from the nopaline synthase gene (NOS-ter) of the Agrobacterium Ti plasmid); it also contains an RK2 origin of replication, a kanamycin resistance gene, and the GUS reporter gene.

Signal Sequences. As noted above, the GUS sequence is replaced (via BamHI/SstI) with a synthetic DNA sequence encoding a peptide signal sequence based on the extensin signal sequences of *Nicotiana plumbaginifolia* and *N. tabacum*

MGKMASLFATFLVVLVSLSLAQTTRVVPVASSAP (SEQ ID NO:14)

The DNA sequence also contains 15 bp of the 5' untranslated region, and restriction sites for Bam HI in its 5'terminus and Sst I in its extreme 3' terminus for insertion into pBI121 in place of GUS. An XmaI restriction site occurs 16 bp upstream from the Sst I site to allow subsequent insertion of EGFP into the plasmid as a Xma I/Sst I fragment.

The sequence underlined above is known to target *N. plumbaginifolia* extensin fusion proteins through the ER and Golgi for post-translational modifications, and finally to the wall. The signal sequence proposed also involves transport of extensins and extensin modules in the same plant family (Solanaceae). Alternatively, one can use the signal sequence from tomato P1 extensin itself

TABLE 1

GFP MUTANTs

| MUTANT | WAVELENGTH (nm) | |
| --- | --- | --- |
| | Excitation | Emitting |
| mGFPX10; F99S, M153T, V163A | Excites at 395 | |
| mGFPX10-5 | Excites at 489 | Emits at 508 |
| GFPA2; I167T | Excites at 471 | |
| GFPB7; Y66H | Excites at 382 | Emits at 440 (blue fluorescence) |
| GFPX10-C7; F99S, M153T, V163A, I167T, S175G | Excites at 395 and 473 | |
| GFPX10-D3; F99S, M153T, V163A, Y66H | Excites at 382 | Emits at 440 |

Addition of GFP. The repetitive HRGP-modules can be expressed as GFP fusion products rather than GUS fusions, and can also be expressed as modules without GFP. Fusion with a green fluorescent protein reporter gene appropriately red-shifted for plant use, e.g. EGFP (an S65T variant recommended for plants by Clontech) or other suitable mutants (see Table 1 above) allows the detection of <700 GFP molecules at the cell surface. GFP requires aerobic conditions for oxidative formation of the fluorophore. It works well at the lower temperatures used for plant cell cultures and normally it does not adversely affect protein function although it may allow the regeneration of plants only when targeted to the ER.

Promoters. As noted above, it is not intended that the present invention be limited by the nature of the promoter(s) used in the expression constructs. The CaMV35S promoter is preferred, although it is not entirely constitutive and expression is "moderate". In some embodiments, higher expression of the constructs is desired to enhance the yield of HRGP modules; in such cases a plasmid with "double" CaMV35S promoters is employed.

D. Selection of Host Cells

A variety of host cells are contemplated (both eukaryotic and prokaryotic). It is not intended that the present invention be limited by the host cells used for expression of the synthetic genes of the present invention. Plant host cells are preferred, including but not limited to legumes (e.g. soy beans) and solanaceous plants (e.g. tobacco).

The present invention is not limited by the nature of the plant cells. All sources of plant tissue are contemplated, including but not limited to seeds. Seeds of flowering plants consist of an embryo, a seed coat, and stored food. When fully formed, the embryo consists basically of a hypocotyl-root axis bearing either one or two cotyledons and an apical meristem at the shoot apex and at the root apex. The cotyledons of most dicots are fleshy and contain the stored food of the seed. In other dicots and most monocots, food is stored in the endosperm and the cotyledons function to absorb the simpler compounds resulting from the digestion of the food.

It is also not intended that the present invention be limited to only certain types of plants. Both monoctyledons and disctyledons are contemplated. Monoctyledons include grasses, lilies, irises, orchids, cattails, palms. Dicotyledons include almost all the familiar trees and shrubs (other than confers) and many of the herbs (non-woody plants).

Tomato cultures are the ideal recipients for repetitive HRGP modules to be hydroxylated and glycosylated: Tomato is readily transformed. The cultures produce cell surface HRGPs in high yields easily eluted from the cell surface of intact cells and they possess the required post-translational enzymes unique to plants—HRGP prolyl hydroxylases, hydroxyproline O-glycosyltransferases and other specific glycosyltransferases for building complex polysaccharide side chains. Furthermore, tomato genetics, and tomato leaf disc transformation/plantlet regeneration are well worked out.

E. Introduction of Nucleic Acid

Expression constructs of the present invention may be introduced into host cells (e.g. plant cells) using methods known in the art. In one embodiment, the expression constructs are introduced into plant cells by particle mediated gene transfer. Particle mediated gene transfer methods are known in the art, are commercially available, and include, but are not limited to, the gas driven gene delivery instrument descried in McCabe, U.S. Pat. No. 5,584,807, the entire contents of which are herein incorporated by reference. This method involves coating the nucleic acid sequence of interest onto heavy metal particles, and accelerating the coated particles under the pressure of compressed gas for delivery to the target tissue.

Other particle bombardment methods are also available for the introduction of heterologous nucleic acid sequences into plant cells. Generally, these methods involve depositing the nucleic acid sequence of interest upon the surface of small, dense particles of a material such as gold, platinum, or tungsten. The coated particles are themselves then coated onto either a rigid surface, such as a metal plate, or onto a carrier sheet made of a fragile material such as mylar. The coated sheet is then accelerated toward the target biological tissue. The use of the flat sheet generates a uniform spread of accelerated particles which maximizes the number of cells receiving particles under uniform conditions, resulting in the introduction of the nucleic acid sample into the target tissue.

Alternatively, an expression construct may be inserted into the genome of plant cells by infecting them with a bacterium, including but not limited to an Agrobacterium strain previously transformed with the nucleic acid sequence of interest. Generally, disarmed Agrobacterium cells are transformed with recombinant Ti plasmids of *Agrobacterium tumefaciens* or Ri plasmids of *Agrobacterium rhizogenes* (such as those described in U.S. Pat. No. 4,940,838, the entire contents of which are herein incorporated by reference) which are constructed to contain the nucleic acid sequence of interest using methods well known in the art (Sambrook, J. et al., (1989) supra). The nucleic acid sequence of interest is then stably integrated into the plant genome by infection with the transformed Agrobacterium strain. For example, heterologous nucleic acid sequences have been introduced into plant tissues using the natural DNA transfer system of *Agrobacterium tumefaciens* and *Agrobacterium rhizogenes* bacteria (for review, see Klee et al. (1987) Ann. Rev. Plant Phys. 38:467–486).

One of skill in the art knows that the efficiency of transformation by Agrobacterium may be enhanced by using a number of methods known in the art. For example, the inclusion of a natural wound response molecule such as acetosyringone (AS) to the Agrobacterium culture has been shown to enhance transformation efficiency with *Agrobac-* terium tumefaciens [Shahla et al. (1987) Plant Molec. Biol. 8:291–298]. Alternatively, transformation efficiency may be enhanced by wounding the target tissue to be transformed. Wounding of plant tissue may be achieved, for example, by punching, maceration, bombardment with microprojectiles, etc. [see, e.g., Bidney et al. (1992) Plant Molec. Biol. 18:301–313].

It may be desirable to target the nucleic acid sequence of interest to a particular locus on the plant genome. Site-directed integration of the nucleic acid sequence of interest into the plant cell genome may be achieved by, for example, homologous recombination using Agrobacterium-derived sequences. Generally, plant cells are incubated with a strain of Agrobacterium which contains a targeting vector in which sequences that are homologous to a DNA sequence inside the target locus are flanked by Agrobacterium transfer-DNA (T-DNA) sequences, as previously described (Offringa et al., (1996), U.S. Pat. No. 5,501,967, the entire contents of which are herein incorporated by reference). One of skill in the art knows that homologous recombination may be achieved using targeting vectors which contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

Where homologous recombination is desired, the targeting vector used may be of the replacement- or insertion-type (Offringa et al. (1996), supra). Replacement-type vectors generally contain two regions which are homologous with the targeted genomic sequence and which flank a heterologous nucleic acid sequence, e.g., a selectable marker gene sequence. Replacement type vectors result in the insertion of the selectable marker gene which thereby disrupts the targeted gene. Insertion-type vectors contain a single region of homology with the targeted gene and result in the insertion of the entire targeting vector into the targeted gene.

Other methods are also available for the introduction of expression constructs into plant tissue, e.g., electroinjection (Nan et al. (1995) In "Biotechnology in Agriculture and Forestry," Ed. Y. P. S. Bajaj, Springer-Verlag Berlin Heidelberg, Vol 34:145–155; Griesbach (1992) HortScience 27:620); fusion with liposomes, lysosomes, cells, minicells or other fusible lipid-surfaced bodies (Fraley et al. (1982) Proc. Natl. Acad. Sci. USA 79:1859–1863; polyethylene glycol (Krens et al. (1982) Nature 296:72–74); chemicals that increase free DNA uptake; transformation using virus, and the like.

In one embodiment, the present invention contemplates introducing nucleic acid via the leaf disc transformation method. Horsch et al. Science 227:1229–1231 (1985). Briefly, disks are punched from the surface of sterilized leaves and submerged with gentle shaking into a culture of A. tumefaciens that had been grown overnight in luria broth at 28° C. The disks are then blotted dry and placed upside-down onto nurse culture plates to induce the regeneration of shoots. Following 2–3 days, the leaf disks are transferred to petri plates containing the same media without feeder cells or filter papers, but in the presence of carbenicillin (500 µg/ml) and kanamycin (300 µg/ml) to select for antibiotic resistance. 2–4 weeks later, the shoots that developed aree removed from calli and placed into root-inducing media with the appropriate antibiotic. These shoots were then further transplanted into soil following the presence of root formation.

EXPERIMENTAL

The following examples serve to illustrate certain preferred embodiments and aspects of the present invention and are not to be construed as limiting the scope thereof.

In the experimental disclosure which follows, the following abbreviations apply: g (gram); mg (milligrams); µg (microgram); M (molar); mM (milliMolar); µM (microMolar); nm (nanometers); L (liter); ml (milliliter); µl (microliters); °C. (degrees Centigrade); m (meter); sec. (second); DNA (deoxyribonucleic acid); cDNA (complementary DNA); RNA (ribonucleic acid); mRNA (messenger ribonucleic acid); X-gal (5-bromo-4-chloro-3-indolyl-β-D-galactopyranoside); LB (Luria Broth), PAGE (polyacrylamide gel electrophoresis); NAA (α-naphtaleneacetic acid); BAP (6-benzyl aminopurine); Tris (tris(hydroxymethyl)-aminomethane); PBS (phosphate buffered saline); 2×SSC (0.3 M NaCl, 0.03 M $Na_3$citrate, pH 7.0); Agri-Bio Inc. (North Miami, Fla.); Analytical Scientific Instruments (Alameda, Calif.); BioRad (Richmond, Calif.); Clontech (Palo Alto Calif.); Delmonte Fresh Produce (Kunia, Hawaii); Difco Laboratories (Detroit, Mich.); Dole Fresh Fruit (Wahiawa, Hawaii); Dynatech Laboratory Inc. (Chantilly Va.); Gibco BRL (Gaithersburg, Md.); Gold Bio Technology, Inc. (St. Louis, Mo.); GTE Corp. (Danvers, Mass.); MSI Corp. (Micron Separations, Inc., Westboro, Mass.); Operon (Operon Technolies, Alameda, Calif.); Pioneer Hi-Bred International, Inc. (Johnston, I A); 5 Prime 3 Prime (Boulder, Colo.); Sigma (St. Louis, Mo.); Promega (Promega Corp., Madison, Wis.); Stratagene (Stratagene Cloning Systems, La Jolla, Calif.); USB (U.S. Biochemical, Cleveland, Ohio).

EXAMPLE 1

Determination of the Peptide Sequence of Acacia Gum Arabic Glycoproteins

In this example, GAGP (SEQ ID NO:15) was isolated and (by using chymotrypsin) the deglycosylated polypeptide backbone was prepared. Although GAGP does not contain the usual chymotryptic cleavage sites, it does contain leucyl and histidyl residues which are occasionally cleaved. Chymotrypsin cleaved sufficient of these "occasionally cleaved" sites to produce a peptide map of closely related peptides.

Purification and Deglycosylation of GAGP (SEQ ID NO:15). GAGP was isolated via preparative Superose-6 gel filtration. Anhydrous hydrogen fluoride deglycosylated it (20 mg powder/mL HF at 4° C., repeating the procedure twice to ensure complete deglycosylation), yielding dGAGP which gave a single symmetrical peak (data not shown) after rechromatography on Superose-6. Further purification of dGAGP by reverse phase chromatography also gave a single major peak, showing a highly biased but constant amino acid composition in fractions sampled across the peak. These data indicated that dGAGP was a single polypeptide component sufficiently pure for sequence analysis.

Sequence Analysis. An incomplete pronase digest gave a large peptide PRP3 which yielded a partial sequence (Table 2) containing all the amino acids present in the suggested dGAGP repeat motif. In view of the limitations of pronase, for further peptide mapping and to obtain more definitive sequence information, dGAGP was digested with chymotrypsin, followed by a two-stage HPLC fractionation scheme. Initial separation of the chymotryptides on a PolySULFOETHYLA$^m$ (designated PSA, PolyLC, Inc. Ellicott City, Md.) cation exchanger yielded three major fractions: S1 and S2 increased with digestion time while S3 showed a concomitant decrease. Further chromatography on PRP-1 resolved PSA fractions S1 and S2 into several peptides.

TABLE 2

AMINO ACID SEQUENCES OF THE GUM ARABIC GLYCOPROTEIN POLYPEPTIDE BACKBONE

| Peptide | Sequence |
| --- | --- |
| S1P5 | Ser-Hyp-Hyp-Hyp-Hyp-Leu-Ser-Hyp-Ser-Leu-Thr-Hyp-Thr-Hyp-Hyp-Leu-Gly-Pro-(Pro) (SEQ ID NO: 16) |
| S1P3 | Ser-Hyp-Hyp-Hyp-Leu-Ser-Hyp-Ser-Hyp-Thr-Hyp-Thr-Hyp-Hyp-Leu-Gly-Pro-(Pro) (SEQ ID NO: 17) |
| S3 | Ser-Hyp-Hyp-Hyp-Thr-Leu-Ser-Hyp-Ser-Hyp-Thr-Hyp-Thr-Hyp-Hyp-Gly-Pro-His-Ser-Hyp-Hyp-Hyp-(Hyp) (SEQ ID NO: 18) |
| S1P2 | Ser-Hyp-Hyp-Hyp-Ser-Leu-Ser-Hyp-Ser-Hyp-Thr-Hyp-Thr-Hyp-Hyp-Thr-Gly-Pro-His (SEQ ID NO: 19) |
| S2P1 | Ser-Hyp-Ser-Hyp-Thr-Hyp-Thr-Hyp-Hyp-Hyp-Gly-Pro-His (SEQ IS NO: 20) |
| S2P2a | Ser-Hyp-Ser-Hyp-Ala-Hyp-Thr-Hyp-Hyp-Leu-Gly-Pro-His (SEQ IS NO: 21) |
| S2P2b | Ser-Hyp-Leu-Pro-Thr-Hyp-Thr-Hyp-Hyp-Leu-Gly-Pro-His (SEQ IS NO: 22) |
| S2P3a | Ser-Hyp-Ser-Hyp-Thr-Hyp-Thr-Hyp-Hyp-Leu-Gly-Pro-His (SEQ IS NO: 23) |
| S2P4 | Ser-Hyp-Hyp-Leu-Thr-Hyp-Thr-Hyp-Hyp-Leu-Gly-Pro-His (SEQ IS NO: 234) |
| S1P4 | Ser-Hyp-Leu-Pro-Thr-Leu-Ser-Hyp-Leu-Pro-Ala/Thr-Hyp-Thr-Hyp-Hyp-Hyp-Gly-Pro-His (SEQ ID NOS: 25 AND 26) |
| Consensus: | (SEQ ID NOS: 27 and 28) Ser-Hyp-Hyp-Hyp-Thr/Hyp-Leu-Ser-Hyp-Ser-Hyp-Thr-Hyp-Thr-Hyp-Hyp-Leu-Gly-Pro-His |

Consensus alternates:
- positions 2,3,4: (Leu)(Pro)(Ser)
- position 5: (Pro)
- positions 7,8,9: (Leu)(Leu)(Ala)
- position 14: (Hyp)
- position 16: (Pro)

Edman degradation showed that these chymotryptides were closely related to each other, to the partial sequence of the large pronase peptide (Table 2), and to the major pronase peptide of GAGP isolated earlier by Delonnay (see above). Indeed, all can be related to a single 19-residue consensus sequence with minor variation in some positions (Table 2). These peptides also reflect the overall amino acid composition and are therefore evidence of a highly repetitive polypeptide backbone with minor variations in the repetitive motif; these include occasional substitution of Leu for Hyp and Ser. Remarkably, fifteen residues of the consensus sequence are "quasi-palindromic" i.e. the side chain sequence is almost the same whether read from the N-terminus or C-terminus.

EXAMPLE 2

Construction of Synthethic HRGP Gene Cassettes

Synthetic gene cassettes encoding contiguous and non-contiguous Hyp modules are constructed using partially overlapping sets consisting of oligonucleotide pairs, "internal repeat pairs" and "external 3'- and 5'-linker pairs" respectively, all with complementary "sticky" ends. The design strategy for the repetitive HRGP modules combines proven approaches described earlier for the production in *E.coli* of novel repetitive polypeptide polymers (McGrath et al. [1990] Biotechnol. Prog. 6:188), of a repetitious synthetic analog of the bioadhesive precursor protein of the mussel *Mytilus edulis,* of a repetitive spider silk protein (Lewis et al. [1996] Protein Express. Purif. 7:400), and of a highly repetitive elastin-like polymer in tobacco [Zhang, X., Urry, D. W., and Daniell, H. "Expression of an environmentally friendly synthetic protein-based polymer gene in transgenic tobacco plants," Plant Cell Reports, 16: 174 (1996)].

The basic design strategy for synthetic HRGP gene cassettes is illustrated by the owing illustrative constructs.

a) Ser-Hyp$_4$ (SEQ ID NO:3) Gene Cassette

A synthetic gene encoding the extensin-like Ser-Hyp$_4$ (SEQ ID NO:3) module is constructed using the following partially overlapping sets of oligonucleotide pairs.

5'-Linker

Amino Acid ( SEQ ID NO:29): A G S S T R A S P (P P P)
5'-GCT GGA TCC TCA ACC CGG GCC TCA CCA (SEQ ID NO:30) CGA CCT AGG AGT TGG GCC CCG AGT GGT GGT GGT GGA-5' (SEQ ID NO:31)

3' Linker (for pBI121-Sig-EGFP)

Amino Acid (SEQ ID NO:32): P P P S P V A R N S P p
5'-CCA CCA CCT TCA CCG GTC GCC CGG AAT TCA CCA CCC (SEQ ID NO:33)
AGT GGC CAG CGG GCC TTA AGT GGT GGG-5' (SEQ ID NO:34)

3' Linker (for pBI121-Sig)

Amino Acid:
5'-CCA CCA CCT TAA TAG AGC TCC CCC (SEQ ID NO:35) ATT ATC TCG AGG GGG-5'(SEQ ID NO:36)

Internal Repeat

Amino Acid (SEQ ID NO:37): P P P S P P P P S P
5'-CCA CCA CCT TCA CCT CCA CCC CCA TCT CCA (SEQ ID NO:38) AGT GGA GGT GGG GGT AGA GGT GGT GGT GGA-5'(SEQ ID NO:39)

Conversion of the "internal" and 5' & 3' "external" gene cassettes to long duplex DNA is accomplished using the following steps:

1. Heat each pair of complementary oligonucleotides to 90° and then anneal by cooling slowly to 60° thereby forming short duplex internal and external DNAs.
2. Combine the 5' external linker duplex with the internal repeat duplexes in an approximately 1:20 molar ratio and anneal by further cooling to yield long duplex DNA capped by the 5' linker. The 5' linker is covalently joined to the internal repeat duplex by ligation using T4 DNA ligase. (Preferrably up to 50, more preferrably up to 30, repeats of the internal repeat duplex can be used).
3. In molar excess, combine the 3' external linker duplex with the above 5' linker-internal repeat duplex, anneal and ligate as described above.
4. Digest the 5' linker-internal repeat-3' linker duplex with BamHI (cuts within the 5'-linker) and EcoR1 (cuts within the 3'-linker).

5. Size fractionate the reaction products using Sephacryl gel permeation chromatography to select constructs greater than 90 bp.
6. Insert the sized, digested synthetic gene cassette into a plasmid having a polylinker containing BamHI and EcoRI sites (e.g., pBluescript SK⁺ or KS⁺ [Stratagene]).
7. Transform *E. coli* cells (e.g., by electroporation or the use of competent cells) with the plasmid into which the synthetic gene construct has been ligated.
8. Following *E. coli* transformation, the internal repeat oligonucleotides are used to screen and identify Ampicillin-resistant colonies carrying the synthetic gene construct.
9. The insert contained on the plasmids within the Ampicillin-resistant colonies are sequenced to confirm the fidelity of the synthtic gene construct.

b) GAGP (SEQ ID NO:15) Consensus Sequence Cassette

A synthetic gene cassette encoding the GAGP consensus sequence is generated as described above using the following 5' linker, internal repeat and 3' linker duplexes.

5'-Linker

Amino Acid (SEQ ID NO:40): A A G S S T R A (S P S)

5'-GCT GCC GGA TCC TCA ACC CGG GCC-3' (SEQ ID NO:41)

3'-CGA CGG CCT AGG AGT TGG GCC CGG AGT GGC AGT-5' (SEQ ID NO:42)

3'-Linker (for pBI121-Sig-EGFP)

Amino Acid (SEQ ID NO:43): S P S P V A R N S PP

5'-TCA CCC TCA CCG GTC GCC CGG AAT TCA CCA CCC-3' (SEQ ID NO:44)

3'GGC CAG CGG GCC TTA AGT GGT GGG-5' (SEQ ID NO:45)

3'-Linker (for pBI121-Sig)

Amino Acid:

5'-TCA CCC TCA TAA TAG AGC TCC CCC-3' (SEQ ID NO:46) 3'ATT ATC TCG AGG GGG-5' (SEQ ID NO:47)

Internal Repeat

Amino Acid (SEQ ID NO:48): S P S P T P T P P P G P H S P P P T L

5'-TCA CCC TCA CCA ACT CCT ACC CCA CCA CCT GGT CCA CAC TCA CCA CCA CCA ACA TTG-3' (SEQ ID NO:49)

3'-GGT TGA GGA TGG GGT GGT GGA CCA GGT GTG AGT GGT GGT GGT TGT AAC AGT GGG AGT-5' (SEQ ID NO:50)

Conversion of the "internal" AGP-like motif and 5' & 3' "external" gene cassettes to long duplex DNA is accomplished using the steps described in section a) above. Up to fifty (50) repeats of the internal repeat duplex are desirable (more preferrably up to thirty (30) repeats, and more preferrably approximately twenty (20) repeats) (i.e., the wild-type protein contains 20 of these repeats).

Since the above GAGP internal repeat is a consensus sequence, it is also desireable to have repeats that comprise a repeat sequence that varies from the consensus sequence (see e.g. Table 2 above). In this regard, the variant sequences are likely to be glycosylated in a slightly different manner, which may confer different properties (e.g. more soluble etc.). Other constructs are shown for other illustrative modules in Table 3.

EXAMPLE 3

Isolation of Tomato P1 Extensin cDNA Clones

In order to obtain the tomato P1 extensin signal sequence (i.e., signal peptide), P1 extensin cDNA clones were isolated using oligonucleotides designed after the P1-unique protein sequence (SEQ ID NO:51): Val-Lys-Pro-Tyr-His-Pro-Thr-Hyp-Val-Tyr-Lys. When present at the N-terminus of a protein sequence, the P1 extensin signal sequence directs the nascent peptide chain to the ER.

EXAMPLE 4

Construction of One Embodiment of an Expression Vector pBI121 is an expression vector which permits the high level expression and secretion of inserted genes in plant cells (e.g., tomato, tobacco, members of the genus Solanace, members of the family Leguminoseae, non-graminaceous monocots). pBI121 contains the 35S CaMV promoter, the tobbaco (*Nicotiana plumbaginifolia*) extensin signal sequence, a EGFP gene, the termination/polyadenylation signal from the nopaline synthetase gene (NOS-ter), a kanamycin-resistance gene (nptII) and the right and left borders of T-DNA to permit transfer into plants by Agrobacterium-mediated transformation.

TABLE 3

ILLUSTRATIVE HRGP SYNTHETIC GENE MODULES

1. MODULES FOR AGP-LIKE SEQUENCES a. The [SP]ₙ Module

| | |
|---|---|
| [SP]ₙ Internal Repeat Oligo's: | 5'-TCA CCC TCA CCA TCT CCT TCG CCA TCA CCC (SEQ ID NO: 52) GGT AGA GGA AGC GGT AGT GGG AGT GGG AGT-5' (SEQ ID NO: 53) |
| The [SP]ₙ 3' & 5' External Linkers for both plasmids are the same as for the GAGP module. | | b. The [AP]ₙ Module

| | |
|---|---|
| [AP]ₙ Internal Repeat Oligo's: | 5'-GCT CCA GCA CCT GCC CCA GCC CCT GCA CCA -3' (SEQ ID NO: 54) GGA CGG GGT CGG GGA CGT GGT -5' (SEQ ID NO: 55) |

TABLE 3-continued

| | |
|---|---|
| [AP]$_n$ External Linker Oligo's for plasmid pBI121-Sig-EGFP | |
| 5'-Linker: | 5'-GCT GCC GGA TCC TCA ACC CGG (SEQ ID NO: 56)<br>3'-CGA CGG CCT AGG AGT TGG GCC CGA GGT CGT-5' (SEQ ID.NO: 57) |
| 3'-Linker: | 5'-GCT CCA GCA CCG GTC GCC CGG AAT TCA CCA CCC-3' (SEQ ID NO: 58)<br>3'-GGC CAG CGG GCC TTA AGT GGT GGG-5' (SEQ ID NO: 59) |
| [AP]$_n$ External 3' Linker Oligos for plasmid pBI121-Sig | 5'-GCT CCA GCA TAA TAG AGC TCC CCC (SEQ ID NO: 60)<br>ATT ATC TCG AGG GGG-5' (SEQ ID NO: 61) | c. The [TP]$_n$ Module

| | |
|---|---|
| [TP]$_n$ Internal Repeat Oligo's:<br>[TP]$_n$ External Linker Oligo's for pBI121-Sig-EGFP: | 5'-ACA CCA ACC CCT ACT CCC ACG CCA ACA CCT ACA CCC ACT CCA (SEQ ID NO: 62)<br>GGA TGA GGG TGC GGT TGT GGA TCT GGG TGA GGT TGT GGT TGG-5' (SEQ ID NO: 63) |
| 5' Linker: | 5'-GCT GCC GGA TCC TCA ACC CGG (SEQ ID NO: 64)<br>3'-CGA CGG CCT AGG AGT TGG GCC TGT GGT TGG-5' (SEQ ID NO: 65) |
| 3' Linker: | 5'-ACA CCA ACC CCG GTC GCC CGG AAT TCA CCA CCC-3' (SEQ ID NO: 66)<br>GGC CAG CGG GCC TTA AGT GGT GGG-5' (SEQ ID NO: 67) |
| [TP]$_n$ External 3' Linker Oligos for pBI121-Sig | 5'-ACA CCA ACC TAA TAG AGC TCC CCC (SEQ ID NO: 68)<br>ATT ATC TCG AGG GGG-5' (SEQ ID NO: 69) |

2. MODULES FOR EXTENSIN-LIKE SEQUENCES a. The [SPP]$_n$ Module

| | |
|---|---|
| [SPP]$_n$ Internal Repeat Oligo's:<br>[SPP]$_n$ External Linkers for pBE121-Sig-EGFP: | 5'-CCA CCA TCA CCA CCC TCT CCT CCA TCA CCC CCA TCC CCA CCA TCA (SEQ ID NO: 70)<br>GGT GGG AGA GGA GGT AGT GGG GGT AGG GGT GGT AGT GGT GGT AGT-5' (SEQ ID NO: 71) |
| 5' Linker: | 5'-GCT GCC GGA TCC TCA ACC CGG GCC (SEQ ID NO: 72)<br>3'-CGA CGG CCT AGG AGT TGG GCC CGG GGT GGT AGT-5' (SEQ ID NO: 73) |
| 3' Linker: | 5'-CCA CCA TCA CCG GTC GCC CGG AAT TCA CCA CCC-3' (SEQ ID NO: 74)<br>GGC CAG CGG GCC TTA AGT GGT GGG-5' (SEQ ID NO: 75) |
| [SPP]$_n$ External 3' Linker for pBE121-Sig: | 5'-CCA CCA TCA TAA TAG AGC TCC CCC (SEQ ID NO: 76)<br>ATT ATC TCG AGG GGG-5' (SEQ ID NO: 77) | b. The [SPPP]$_n$ Module

| | |
|---|---|
| [SPPP]$_n$ Internal Repeat Oligo's: | 5'- CCA CCA CCT TCA CCA CCT TCA TCT CCC CCA CCT TCC CCT CCA CCA TCA (SEQ ID NO: 78)<br>AGT GGT GGA GGT AGA GGG GGT GGA AGG GGA GGT GGT AGT GGT GGT GGA-5'<br>(SEQ ID NO: 79) |
| [SPPP]$_n$ External Linker Oligo's for pBI121-Sig-EGFP: | |
| 5'-Linker: | 5'-GCT GGA TCC TCA ACC CGG GCC TCA (SEQ ID NO: 80)<br>3'-CGA CCT AGG AGT TGG GCC CGG AGT GGT GGT GGA-5' (SEQ ID NO: 81) |
| 3'-Linker: | 5'-CCA CCA CCT TCA CCG GTC GCC CGG AAT TCA CCA CCC-3' (SEQ ID NO: 82)<br>AGT GGC CAG CGG GCC TTA AGT GGT GGG-5' (SEQ ID NO: 83) |
| [SPPP]$_n$ External 3' Linker Oligos for pBI121-Sig: | 5'-CCA CCA CCT TAA TAG AGC TCC CCC (SEQ ID NO: 84)<br>ATT ATC TCG AGG GGG-5' (SEQ ID NO: 85) | d. The P3-Type Extensin Palindromic Module:

| | |
|---|---|
| P3-Type Extensin Palindromic Internal Repeat Oligo's:<br>P3-Type Extensin Palindromic External Linker Oligo's: | 5'-CCA CCA CCT TCA CCC TCT CCA CCT CCA CCA TCT CCG TCA CCA (SEQ ID NO: 86)<br>AGT GGG AGA GGT GGA GGT GGT AGA GGC AGT GGT GGT GGT GGA-5' (SEQ ID NO: 87)<br>Use the [SPPP]$_n$ linkers (SEE ABOVE) | e. The Potato Lectin HRGP Palindromic Module:

| | |
|---|---|
| Potato Lectin HRGP Palindromic External Linker Oligo's:<br>Potato Lectin HRGP Palindromic External | 5'-CCA CCA CCT TCA CCC CCA TCT CCA CCT CCA CCA TCT CCA CCG TCA CCA<br>(SEQ ID NO: 88)<br>AGT GGG GGT AGA GGT GGA GGT GGT AGA GGT GGC AGT GGT GGT GGT GGA-5'<br>(SEQ ID NO: 89)<br>Use the [SPPP]$_n$ linkers (SEE ABOVE) |

TABLE 3-continued

Linker Oligo's:

f. P1-Extensin-Like Modules:

i. The SPPPPTPVYK Module:

| | |
|---|---|
| SPPPPTPVYK Internal Repeat Oligo's: | 5'-CCA CCA CCT ACT CCC GTT TAC AAA TCA CCA CCA CCA CCT ACT CCC GTT TAC AAA TCA CCA (SEQ ID NO: 90)<br>TGA GGG CAA ATG TTT AGT GGT GGT GGT GGA TCA GGG CAA ATG TTT AGT GGT GGT GGT GGA-5' (SEQ ID NO: 91) |
| SPPPPTPVYK External Linker Oligo's: | Use the [SPPP]$_n$ linkers (SEE ABOVE) | ii. The SPPPPVKPYHPTPVFL Module:

| | |
|---|---|
| SPPPPVKPYHPTPVFL Internal Repeat Oligo's: | 5'-CCA CCA CCT GTC AAG CCT TAC CAC CCC ACT CCC GTT TTT CTT TCA CCA (SEQ ID NO: 92)<br>CAG TTC GGA ATG GTG GGG TGA GGG CAA AAA GAA AGT GGT GGT GGT GGA-5' (SEQ ID NO: 93) |
| SPPPPVKPYHPTPVFL External Linker Oligo's: | Use the [SPPP]$_n$ linkers (SEE ABOVE) | iii. The SPPPPVLPFHPTPVYK Module:

| | |
|---|---|
| SPPPPVLPFHPTPVYK Internal Repeat Oligo's: | 5'-CCA CCA CCT GTC TTA CCT TTC CAC CCC ACT CCC GTT TAC AAA TCA CCA (SEQ ID NO: 94)<br>CAG AAT GGA AAG GTG GGG TGA GGG CAA ATG TTT AGT GGT GGT GGT GGA-5' (SEQ ID NO: 95) |
| SPPPPVLPFHPTPVYK External Linker Oligo's: | Use the [SPPP]$_n$ linkers (SEE ABOVE) |
| EGFP 3' Linker Oligo's needed to insert EGFP into pBI121-Sig-EGF | 5'-GGC CGC GAG CTC CAG CAC GGG (SEQ ID NO: 96)<br>CG CTC GAG GTC GTG CCC-5' (SEQ ID NO: 97) |

The presence of the extensin signal sequence at the N-terminus of proteins encoded by genes inserted into the pBI121 expression vector (e.g., HRGPs encoded by synthtic gene constructs). The tobacco signal sequence was demonstrated to target extensin fusion proteins through the ER and Golgi for posttranslational modifications, and finally to the wall. The targeted expression of recombinant HRGPs is not dependent upon the use of the tobacco extensin signal sequence. Signal sequences involved in the transport of extensins and extensin modules in the same plant family (Solanaceae) as tobacco may be employed; alternatively, the signal sequence from tomato P1 extensin may be employed.

The EGFP gene encodes a green fluorescent protein (GFP) appropriately red-shifted for plant use (the EGFP gene encodes a S65T variant optimized for use in plants and is available from Clontech). Other suitable mutants may be employed (see Table 1). These modified GFPs allow the detection of less than 700 GFP molecules at the cell surface. The use of a GFP gene provides a reporter gene and permits the formation of fusion proteins comprising repetitive HRGP modules. GFPs require aerobic conditions for oxidative formation of the fluorophore. It is functional at the lower temperatures used for plant cell cultures, normally it does not adversely affect protein function.

Plasmids pBI121-Sig and pBI121-Sig-EGFP are constructed as follows. For both plasmids, the GUS gene present in pBI121 (Clontech) is deleted by digestion with BamHI and SstI and a pair of partially complemetary oligonucleotides encoding the tobacco extensin signal sequence is annealed to the BamHI and SstI ends. The oligonucleotides encoding the 21 amino acid extensin signal sequence have the following sequence: 5'-GA TCC GCA ATG GGA AAA ATG GCT TCT CTA TTT GCC ACA TTT TTA GTG GTT TTA GTG TCA CTT AGC TTA GCA CAA ACA ACC CGG GTA CCG GTC GCC ACC ATG GTG TAA AGC GGC CGC GAG CT-3' (SEQ ID NO:98) and 5'-C GCG GCC GCT TTA CAC CAT GGT GGC GAC CGG TAC CCG GGT TGT TTG TGC TAA GCT AAG TGA CAC TAA AAC CAC TAA AAA TGT GGC AAA TAG AGA AGC CAT TTT TCC CAT TGC G-3' (SEQ ID NO:99). In addition to encoding the extensin signal sequence, this pair of oligonucleotides, when inserted into the digested pBI121 vector, provides a BamHI site (5' end) and XmaI and SstI sites (3' end). The XmaI and SstI sites allow the insertion of the GFP gene. The modified pBI121 vector lacking the GUS gene and containing the synthetic extensin signal sequence is termed pBI121-Sig. Proper construction of pBI121 is confirmed by DNA sequencing.

The GFP gene (e.g., the EGFP gene) is inserted into pBI121-Sig to make pBI121-Sig-EGFP as follows. The EGFP gene is excised from pEGFP (Clontech) as a 1.48 kb XmaI/NotI fragment (base pairs 270 to 1010 in pEGFP). This 1.48 kb XmaI/NotI fragment is then annealed and ligated to a synthetic 3' linker (see above). The EGFP-3' linker is then digested with SstI to produce an XmaI/SstI EGFP fragment which in inserted into the XmaI/SstI site of pBI121-Sig to create pBI121-Sig-EGFP. The AgeI (discussed below), XmaI and SstI sites provide unique restriction enzyme sites. Proper construction of the plasmids is confirmed by DNA sequencing.

The EGFP sequences in pBI121-Sig-EGFP contain an AgeI site directly before the translation start codon (i.e., ATG) of EGFP. Synthtic HRGP gene cassettes are inserted into the plasmid between the signal sequence and the EGFP gene sequences as XmaI/AgeI fragments; the HRGP gene cassettes are excised as XmaI/AgeI fragments from the pBluescript constructs described in Ex.2. Proper construction of HRGP-containing expression vectors is confirmed by DNA sequencing and/or restriction enzyme digestion.

Expression of the synthethic HRGP gene cassettes is not dependent upon the use of the pBI121-Sig and pBI121-Sig- EGFP gene cassette. Analogous expression vectors containing other promoter elements functional in plant cells may be employed (e.g., the CaMV region IV promoter, ribulose-1, 6-biphosphate (RUBP) carboxylase small subunit (ssu) promoter, the nopaline promoter, octopine promoter, mannopine promoter, the β-conglycinin promoter, the ADH promoter, heat shock promoters, tissue-specific promoters, e.g., promoters associated with fruit ripening, promoters regulated during seed ripening (e.g., promoters from the napin, phaseolin and glycinin genes). For example, expression vectors containing a promoter that directs high level expression of inserted gene sequences in the seeds of plants (e.g., fruits, legumes and cereals, including but not limited to corn, wheat, rice, tomato, potato, yam, pepper, squash cucumbers, beans, peas, apple, cherry, peach, black locust, pine and maple trees) may be employed. Expression may also be carried out in green algae.

In addition, alternative reporter genes may be employed in place of the GFP gene. Suitable reporter genes include β-glucuronidase (GUS), neomycin phosphotransferase II gene (nptII), alkaline phosphatase, luciferase, CAT (Chloramphenicol AcetylTransferase). Preferred reporter genes lack Hyp residues. Further, the proteins encoded by the synthetic HRGP genes need not be expressed as fusion proteins. This is readily accomplished using the the pBI121-Sig vector.

EXAMPLE 5

Expression of Recombinant HRGPs in Tomato Cell Suspension Cultures

The present invention contemplates recombinant HRGPs encoded by expression vectors comprising synthetic HRGP gene modules are expressed in tomato cell suspension cultures. The expression of recombinant HRGPs in tomato cell suspension cultures is illustrated by the discussion provided below for recombinant GAGP expression.

a) Expression of Recombinant GAGP

An expression vector containing the synthetic GAGP gene cassette (capable of being expressed as a fusion with GFP or without GFP sequences) is introduced into tomato cell suspension cultures. A variety of means are known to the art for the transfer of DNA into tomato cell suspension cultures, including Agrobacterium-mediated transfer and biolistic transformation.

Agrobacterium-mediated transformation: The present invention contemplates transforming both suspension cultured cells (Bonnie Best cultures) and tomato leaf discs by mobilizing the above-described plasmid constructions (and others) from *E. coli* into *Agrobacterium tumefaciens* strain LBA4404 via triparental mating. Positive colonies are used to infect tomato cultures or leaf discs (*Lysopersicon esculentum*). Transformed cells/plants are selected on MSO medium containing 500 mg/mL carbenicillin and 100 mg/mL kanamycin. Expression of GFP fusion products are conveniently monitored by fluoresence microscopy using a high Q FITC filter set (Chroma Technology Corp.). FITC conjugates (e.g. FITC-BSA) can be used along with purified recombinant GFP as controls for microscopy set-up. Cultured tomato cells show only very weak autofluorescence. Thus, one can readily verify the spatiotemporal expression of GFP-Hyp module fusion products.

Transgenic cells/plants can be examined for transgene copy number and construct fidelity genomic Southern blotting and for the HRGP construct mRNA by northern blotting, using the internal repeat oligonucleotides as probes. Controls include tissue/plants which are untransformed, transformed with the pBI121 alone, pBI121 containing only GFP, and pBI121 having the signal sequence and GFP but no HRGP synthetic gene.

Microprojectile bombardment: 1.6 M gold particles are coated with each appropriate plasmid construct DNA for use in a Biolistic particle delivery system to transform the tomato suspension cultures/callus or other tissue. Controls include: particles without DNA, particles which contain PBI121 only, and particles which contain PBI121 and GFP.

b) Expression of Other HRGPs Of Interest

As noted above, the present invention contemplates expressing a variety of HRGPs, fragments and variants. Such HRGPs include, but are not limited to, RPRps, extensins, AGPs and other plant gums (e.g. gum Karaya, gum Tragacanth, gum Ghatti, etc.). HRGP chimeras include but are not limited to HRGP plant lectins, including the solanaceous lectins, plant chitinases, and proteins in which the HRGP portion serves as a spacer (such as in sunflower). The present invention specifically contemplates using the HRGP modules (described above) as spacers to link non-HRGP proteins (e.g. enzymes) together.

From the above, it should be clear that the present invention provides a new approach and solution to the problem of producing plant gums. The approach is not dependent on environmental factors and greatly simplifies production of a variety of naturally-occurring gums, as well as designer gums.

---

I claim:

1. An isolated plant gum polynucleotide sequence encoding a polypeptide sequence of between thirteen and nineteen amino acids, wherein said polypeptide sequence comprises a first sequence and a second sequence, said first sequence consisting of Ser-Hyp-Hyp-Hyp-X (SEQ ID NO:100), wherein X is selected from Hyp and Thr, and said second sequence consisting of Xaa-Hyp-Xaa-Xyp (SEQ ID NO:101), wherein Xaa is an amino acid other than hydroxyproline, wherein said first sequence is repeated at least once in said polypeptide sequence.

2. An isolated plant gum polynucleotide sequence encoding a polypeptide sequence of between thirteen and nineteen amino acids, wherein said polypeptide sequence comprises a first sequence and a second sequence, said first sequence consisting of Ser-Hyp-Hyp-Hyp-X (SEQ ID NO:100), wherein X is selected from Hyp and Thr, and said second sequence consisting of Ser-Hyp-Ser-Hyp (SEQ ID NO:102), wherein said polypeptide sequence further comprises a third sequence consisting of Thr-Hyp-Thr-Hyp-Hyp-Hyp (SEQ ID NO:103).

3. The polynucleotide sequence of claim 2, wherein said polypeptide sequence is selected from the group consisting of SEQ ID NO:1 and SEQ ID NO:2.

4. An isolated polynucleotide sequence encoding a polypeptide sequence of between thirteen and nineteen amino acids, wherein said polypeptide sequence is X-Hyp-Hyp-Hyp-X-X-Ser-Hyp-Ser-Hyp-Thr-Hyp-Thr-Hyp-Hyp-Hyp-X-Y-Z (SEQ ID NO:104), wherein X is Leu or nothing, Y is Pro or nothing, and Z is His or nothing.

5. An expression vector comprising said polynucleotide sequence of claim 4.

6. The vector of claim 5, further comprising a promoter operably linked to said polynucleotide sequence.

7. The vector of claim 6, wherein said promoter is a viral promoter.

8. The vector of claim 7, wherein said viral promoter is selected from the group consisting of the 35S and 19S RNA promoters of cauliflower mosaic virus.

9. The vector of claim 5, further comprising an extensin signal sequence.

10. The vector of claim 5, further comprising a reporter gene.

11. The vector of claim 10, wherein said reporter gene is the GFP gene.

12. A host cell comprising the vector of claim 5.

13. The host cell of claim 12, wherein said host cell is a plant cell.

14. The plant cell of claim 13, wherein said plant cell expresses a glycoprotein comprising said polypeptide sequence.

15. A method for producing a glycoprotein, comprising:
 a) providing,
  i) an expression vector comprising the polynucleotide sequence of claim 4, and
  ii) a host cell; and
 b) introducing said vector into said host cell under conditions suitable for the expression of the glycoprotein encoded by said polynucleotide sequence of claim 4.

16. The method of claim 15, wherein said host cell is growing in culture.

17. The method of claim 16, further comprising the step of:
 c) recovering said glycoprotein from said host cell culture.

18. The method of claim 16, wherein said host cell is a plant cell.

19. The method of claim 18, wherein said plant cell is derived from a plant selected from the family Leguminoseae.

* * * * *

UNITED STATES PATENT AND TRADEMARK OFFICE
CERTIFICATE OF CORRECTION

PATENT NO. : 6,570,062 B1 Page 1 of 1
DATED : May 27, 2003
INVENTOR(S) : Marcia J. Kieliszewski It is certified that error appears in the above-identified patent and that said Letters Patent is hereby corrected as shown below:

<u>Title page,</u>
Items [12] and [75], please change "Kielszewski" to read as follows:
-- [12]  **United States Patent
    Kieliszewski**

[75]  Inventor: Marcia J. Kieliszewski, Albany, OH (US) --

Signed and Sealed this

Tenth Day of February, 2004

JON W. DUDAS
*Acting Director of the United States Patent and Trademark Office*

SEQUENCE LISTING (1) GENERAL INFORMATION:

(iii) NUMBER OF SEQUENCES: 106

(2) INFORMATION FOR SEQ ID NO:1:

(i) SEQUENCE CHARACTERISTICS:
      (A) LENGTH: 19 amino acids
      (B) TYPE: amino acid
      (C) STRANDEDNESS: Not Relevant
      (D) TOPOLOGY: unknown (ii) MOLECULE TYPE: protein

```
    (ix) FEATURE:
          (A) NAME/KEY: Modified-site
          (B) LOCATION: 2..5
          (D) OTHER INFORMATION: /note= "The Proline at these
              positions is a hydroxyproline."

(ix) FEATURE:
          (A) NAME/KEY: Modified-site
          (B) LOCATION: 8
          (D) OTHER INFORMATION: /note= "The Proline at this
              position is a hydroxyproline."

(ix) FEATURE:
          (A) NAME/KEY: Modified-site
          (B) LOCATION: 10
          (D) OTHER INFORMATION: /note= "The Proline at this
              position is a hydroxyproline."

(ix) FEATURE:
          (A) NAME/KEY: Modified-site
          (B) LOCATION: 12
          (D) OTHER INFORMATION: /note= "The Proline at this
              position is a hydroxyproline."

(ix) FEATURE:
          (A) NAME/KEY: Modified-site
          (B) LOCATION: 14..16
          (D) OTHER INFORMATION: /note= "The Proline at these
              positions is a hydroxyproline."

(xi) SEQUENCE DESCRIPTION: SEQ ID NO:1:

Ser Pro Pro Pro Pro Leu Ser Pro Ser Pro Thr Pro Thr Pro Pro Pro
1               5                  10                 15

Gly Pro His (2) INFORMATION FOR SEQ ID NO:2:

(i) SEQUENCE CHARACTERISTICS:
          (A) LENGTH: 19 amino acids
          (B) TYPE: amino acid
          (C) STRANDEDNESS: Not Relevant
          (D) TOPOLOGY: unknown (ii) MOLECULE TYPE: protein (ix) FEATURE:
          (A) NAME/KEY: Modified-site
          (B) LOCATION: 2..4
          (D) OTHER INFORMATION: /note= "The Proline at these
              positions is a hydroxyproline."

(ix) FEATURE:
          (A) NAME/KEY: Modified-site
          (B) LOCATION: 8
          (D) OTHER INFORMATION: /note= "The Proline at this
              position is a hydroxyproline."

(ix) FEATURE:
          (A) NAME/KEY: Modified-site
          (B) LOCATION: 10
          (D) OTHER INFORMATION: /note= "The Proline at this
              position is a hydroxyproline."

(ix) FEATURE:
          (A) NAME/KEY: Modified-site
          (B) LOCATION: 12
          (D) OTHER INFORMATION: /note= "The Proline at this
              position is a hydroxyproline."

(ix) FEATURE:
          (A) NAME/KEY: Modified-site
          (B) LOCATION: 14..16
          (D) OTHER INFORMATION: /note= "The Proline at these
              positions is a hydroxyproline."

(xi) SEQUENCE DESCRIPTION: SEQ ID NO:2:
```

```
Ser Pro Pro Pro Thr Leu Ser Pro Ser Pro Thr Pro Thr Pro Pro Pro
1               5                   10                  15
Gly Pro His
```

(2) INFORMATION FOR SEQ ID NO:3:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: unknown (ii) MOLECULE TYPE: protein (ix) FEATURE:
        (A) NAME/KEY: Modified-site
        (B) LOCATION: 2..5
        (D) OTHER INFORMATION: /note= "The Proline at these
            positions is a hydroxyproline."

(xi) SEQUENCE DESCRIPTION: SEQ ID NO:3:

```
Ser Pro Pro Pro Pro
1               5
```

(2) INFORMATION FOR SEQ ID NO:4:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: unknown (ii) MOLECULE TYPE: protein (ix) FEATURE:
        (A) NAME/KEY: Modified-site
        (B) LOCATION: 2
        (D) OTHER INFORMATION: /note= "The Proline at this
            position is a hydroxyproline."

(xi) SEQUENCE DESCRIPTION: SEQ ID NO:4:

```
Pro Pro Val Tyr Lys
1               5
```

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: unknown (ii) MOLECULE TYPE: protein (ix) FEATURE:
        (A) NAME/KEY: Modified-site
        (B) LOCATION: 1
        (D) OTHER INFORMATION: /note= "Xaa can be Thr, Glu,
            hydroxyproline, Pro, His and Ile."

(ix) FEATURE:
        (A) NAME/KEY: Modified-site
        (B) LOCATION: 2
        (D) OTHER INFORMATION: /note= "The Proline at position 2
            is a hydroxyproline."

(xi) SEQUENCE DESCRIPTION: SEQ ID NO:5:

```
Xaa Pro Val Tyr Lys
1               5
```

(2) INFORMATION FOR SEQ ID NO:6:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: unknown (ii) MOLECULE TYPE: protein (ix) FEATURE:
        (A) NAME/KEY: Modified-site
        (B) LOCATION: 2
        (D) OTHER INFORMATION: /note= "The Proline at this
            position is a hydroxyproline."

(ix) FEATURE:
        (A) NAME/KEY: Modified-site
        (B) LOCATION: 4
        (D) OTHER INFORMATION: /note= "Xaa can be Thr, Glu,
            hydroxyproline, Pro, His and Ile."

(xi) SEQUENCE DESCRIPTION: SEQ ID NO:6:

Pro Pro Val Xaa Lys
1               5

(2) INFORMATION FOR SEQ ID NO:7:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: unknown (ii) MOLECULE TYPE: protein (ix) FEATURE:
        (A) NAME/KEY: Modified-site
        (B) LOCATION: 3
        (D) OTHER INFORMATION: /note= "Xaa can be Thr, Glu,
            hydroxyproline, Pro, His and Ile."

(xi) SEQUENCE DESCRIPTION: SEQ ID NO:7:

Pro Pro Xaa Tyr Lys
1               5

(2) INFORMATION FOR SEQ ID NO:8:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: unknown (ii) MOLECULE TYPE: protein (ix) FEATURE:
        (A) NAME/KEY: Modified-site
        (B) LOCATION: 3
        (D) OTHER INFORMATION: /note= "Xaa can be Thr, Glu,
            hydroxproline, Pro, His and Ile."

(ix) FEATURE:
        (A) NAME/KEY: Modified-site
        (B) LOCATION: 5
        (D) OTHER INFORMATION: /note= "Xaa can be Thr, Glu,
            hydroxyproline, Pro, His and Ile."

(xi) SEQUENCE DESCRIPTION: SEQ ID NO:8:

Pro Pro Xaa Tyr Xaa
1               5

(2) INFORMATION FOR SEQ ID NO:9:

```
    (i) SEQUENCE CHARACTERISTICS:
        (A) LENGTH: 4 amino acids
        (B) TYPE: amino acid
        (C) STRANDEDNESS: Not Relevant
        (D) TOPOLOGY: unknown (ii) MOLECULE TYPE: protein (ix) FEATURE:
        (A) NAME/KEY: Modified-site
        (B) LOCATION: 1
        (D) OTHER INFORMATION: /note= "Xaa can be Thr, Glu,
            hydroxyproline, Pro, His and Ile."

(ix) FEATURE:
        (A) NAME/KEY: Modified-site
        (B) LOCATION: 3
        (D) OTHER INFORMATION: /note= "Xaa can be Thr, Glu,
            hydroxyproline, Pro, His and Ile."

(xi) SEQUENCE DESCRIPTION: SEQ ID NO:9:

Xaa Pro Xaa Pro
1

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:10:

CCACCACCTT CACCTCCACC CCCATCTCCA                                     30

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:11:

TCACCATCAC CATCTCCTTC GCCATCACCC                                     30

(2) INFORMATION FOR SEQ ID NO:12:

(i) SEQUENCE CHARACTERISTICS:
        (A) LENGTH: 123 base pairs
        (B) TYPE: nucleic acid
        (C) STRANDEDNESS: double
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:12:

GCTGGATCCT CAACCCGGGC CTCACCACCA CCACCTTCAC CTCCACCCCC ATCTCCACCA    60

CCACCTTCAC CTCCACCCCC ATCTCCACCA CCACCTTCAC CGGTCGCCCG GAATTCACCA  120

CCC                                                                123
```

```
(2) INFORMATION FOR SEQ ID NO:13:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:13:

Ser Pro Ser Pro Thr Pro Thr Pro Pro Pro Gly Pro
 1               5                  10

(2) INFORMATION FOR SEQ ID NO:14:

(i) SEQUENCE CHARACTERISTICS:
        (A) LENGTH: 34 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:14:

Met Gly Lys Met Ala Ser Leu Phe Ala Thr Phe Leu Val Val Leu Val
 1               5                  10                  15

Ser Leu Ser Leu Ala Gln Thr Thr Arg Val Val Pro Val Ala Ser Ser
                20                  25                  30

Ala Pro (2) INFORMATION FOR SEQ ID NO:15:

(i) SEQUENCE CHARACTERISTICS:
        (A) LENGTH: 4 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:15:

Gly Ala Gly Pro
 1

(2) INFORMATION FOR SEQ ID NO:16:

(i) SEQUENCE CHARACTERISTICS:
        (A) LENGTH: 18 amino acids
        (B) TYPE: amino acid
        (C) STRANDEDNESS: Not Relevant
        (D) TOPOLOGY: unknown (ii) MOLECULE TYPE: protein (ix) FEATURE:
        (A) NAME/KEY: Modified-site
        (B) LOCATION: 2..5
        (D) OTHER INFORMATION: /note= "The Proline at these
            positions is a hydroxyproline."

(ix) FEATURE:
        (A) NAME/KEY: Modified-site
        (B) LOCATION: 8
        (D) OTHER INFORMATION: /note= "The Proline at this
            position is a hydroxyproline."

(ix) FEATURE:
        (A) NAME/KEY: Modified-site
        (B) LOCATION: 12
        (D) OTHER INFORMATION: /note= "The Proline at this
```

```
                    position is a hydroxyproline."

(ix) FEATURE:
         (A) NAME/KEY: Modified-site
         (B) LOCATION: 14..15
         (D) OTHER INFORMATION: /note= "The Proline at these
             positions is a hydroxyproline."

(xi) SEQUENCE DESCRIPTION: SEQ ID NO:16:

Ser Pro Pro Pro Pro Leu Ser Pro Ser Leu Thr Pro Thr Pro Pro Leu
1               5                   10                  15

Gly Pro (2) INFORMATION FOR SEQ ID NO:17:

(i) SEQUENCE CHARACTERISTICS:
         (A) LENGTH: 18 amino acids
         (B) TYPE: amino acid
         (C) STRANDEDNESS: Not Relevant
         (D) TOPOLOGY: unknown (ii) MOLECULE TYPE: protein (ix) FEATURE:
         (A) NAME/KEY: Modified-site
         (B) LOCATION: 2..5
         (D) OTHER INFORMATION: /note= "The Proline at these
             positions is a hydroxyproline."

(ix) FEATURE:
         (A) NAME/KEY: Modified-site
         (B) LOCATION: 8
         (D) OTHER INFORMATION: /note= "The Proline at this
             position is a hydroxyproline."

(ix) FEATURE:
         (A) NAME/KEY: Modified-site
         (B) LOCATION: 10
         (D) OTHER INFORMATION: /note= "The Proline at this
             position is a hydroxyproline."

(ix) FEATURE:
         (A) NAME/KEY: Modified-site
         (B) LOCATION: 12
         (D) OTHER INFORMATION: /note= "The Proline at this
             position is a hydroxyproline."

(ix) FEATURE:
         (A) NAME/KEY: Modified-site
         (B) LOCATION: 14..15
         (D) OTHER INFORMATION: /note= "The Proline at these
             positions is a hydroxyproline."

(xi) SEQUENCE DESCRIPTION: SEQ ID NO:17:

Ser Pro Pro Pro Pro Leu Ser Pro Ser Pro Thr Pro Thr Pro Pro Leu
1               5                   10                  15

Gly Pro (2) INFORMATION FOR SEQ ID NO:18:

(i) SEQUENCE CHARACTERISTICS:
         (A) LENGTH: 23 amino acids
         (B) TYPE: amino acid
         (C) STRANDEDNESS: Not Relevant
         (D) TOPOLOGY: unknown (ii) MOLECULE TYPE: protein (ix) FEATURE:
         (A) NAME/KEY: Modified-site
         (B) LOCATION: 2..4
         (D) OTHER INFORMATION: /note= "The Proline at these
             positions is a hydroxyproline."
```

```
    (ix) FEATURE:
         (A) NAME/KEY: Modified-site
         (B) LOCATION: 8
         (D) OTHER INFORMATION: /note= "The Proline at this
             position is a hydroxyproline."

(ix) FEATURE:
         (A) NAME/KEY: Modified-site
         (B) LOCATION: 10
         (D) OTHER INFORMATION: /note= "The Proline at this
             position is a hydroxyproline."

(ix) FEATURE:
         (A) NAME/KEY: Modified-site
         (B) LOCATION: 12
         (D) OTHER INFORMATION: /note= "The Proline at this
             position is a hydroxyproline."

(ix) FEATURE:
         (A) NAME/KEY: Modified-site
         (B) LOCATION: 14..16
         (D) OTHER INFORMATION: /note= "The Proline at these
             positions is a hydroxyproline."

(ix) FEATURE:
         (A) NAME/KEY: Modified-site
         (B) LOCATION: 21..23
         (D) OTHER INFORMATION: /note= "The Proline at these
             positions is a hydroxyproline."

(xi) SEQUENCE DESCRIPTION: SEQ ID NO:18:

Ser Pro Pro Pro Thr Leu Ser Pro Ser Pro Thr Pro Thr Pro Pro Pro
1               5                   10                  15

Gly Pro His Ser Pro Pro Pro
            20

(2) INFORMATION FOR SEQ ID NO:19:

(i) SEQUENCE CHARACTERISTICS:
         (A) LENGTH: 19 amino acids
         (B) TYPE: amino acid
         (C) STRANDEDNESS: Not Relevant
         (D) TOPOLOGY: unknown (ii) MOLECULE TYPE: protein (ix) FEATURE:
         (A) NAME/KEY: Modified-site
         (B) LOCATION: 2..4
         (D) OTHER INFORMATION: /note= "The Proline at these
             positions is a hydroxyproline."

(ix) FEATURE:
         (A) NAME/KEY: Modified-site
         (B) LOCATION: 8
         (D) OTHER INFORMATION: /note= "The Proline at this
             position is a hydroxyproline."

(ix) FEATURE:
         (A) NAME/KEY: Modified-site
         (B) LOCATION: 10
         (D) OTHER INFORMATION: /note= "The Proline at this
             position is a hydroxyproline."

(ix) FEATURE:
         (A) NAME/KEY: Modified-site
         (B) LOCATION: 12
         (D) OTHER INFORMATION: /note= "The Proline at this
             position is a hydroxyproline."

(ix) FEATURE:
         (A) NAME/KEY: Modified-site
         (B) LOCATION: 14..15
         (D) OTHER INFORMATION: /note= "The Proline at these
             positions is a hydroxyproline."
```

(xi) SEQUENCE DESCRIPTION: SEQ ID NO:19:

Ser Pro Pro Pro Ser Leu Ser Pro Ser Pro Thr Pro Thr Pro Thr
1               5                  10                  15

Gly Pro His (2) INFORMATION FOR SEQ ID NO:20:

(i) SEQUENCE CHARACTERISTICS:
         (A) LENGTH: 13 amino acids
         (B) TYPE: amino acid
         (C) STRANDEDNESS: Not Relevant
         (D) TOPOLOGY: unknown (ii) MOLECULE TYPE: protein (ix) FEATURE:
         (A) NAME/KEY: Modified-site
         (B) LOCATION: 2
         (D) OTHER INFORMATION: /note= "The Proline at this
             position is a hydroxyproline."

(ix) FEATURE:
         (A) NAME/KEY: Modified-site
         (B) LOCATION: 4
         (D) OTHER INFORMATION: /note= "The Proline at this
             position is a hydroxyproline."

(ix) FEATURE:
         (A) NAME/KEY: Modified-site
         (B) LOCATION: 6
         (D) OTHER INFORMATION: /note= "The Proline at this
             position is a hydroxyproline."

(ix) FEATURE:
         (A) NAME/KEY: Modified-site
         (B) LOCATION: 8..10
         (D) OTHER INFORMATION: /note= "The Proline at these
             positions is a hydroxyproline."

(xi) SEQUENCE DESCRIPTION: SEQ ID NO:20:

Ser Pro Ser Pro Thr Pro Thr Pro Pro Pro Gly Pro His
1               5                  10

(2) INFORMATION FOR SEQ ID NO:21:

(i) SEQUENCE CHARACTERISTICS:
         (A) LENGTH: 13 amino acids
         (B) TYPE: amino acid
         (C) STRANDEDNESS: Not Relevant
         (D) TOPOLOGY: unknown (ii) MOLECULE TYPE: protein (ix) FEATURE:
         (A) NAME/KEY: Modified-site
         (B) LOCATION: 2
         (D) OTHER INFORMATION: /note= "The Proline at this
             position is a hydroxyproline."

(ix) FEATURE:
         (A) NAME/KEY: Modified-site
         (B) LOCATION: 4
         (D) OTHER INFORMATION: /note= "The Proline at this
             position is a hydroxyproline."

(ix) FEATURE:
         (A) NAME/KEY: Modified-site
         (B) LOCATION: 6
         (D) OTHER INFORMATION: /note= "The Proline at this
             position is a hydroxyproline."

(ix) FEATURE:
         (A) NAME/KEY: Modified-site

```
          (B) LOCATION: 8..9
          (D) OTHER INFORMATION: /note= "The Proline at these
              positions is a hydroxyproline."

(xi) SEQUENCE DESCRIPTION: SEQ ID NO:21:

Ser Pro Ser Pro Ala Pro Thr Pro Pro Leu Gly Pro His
 1               5                  10

(2) INFORMATION FOR SEQ ID NO:22:

(i) SEQUENCE CHARACTERISTICS:
          (A) LENGTH: 13 amino acids
          (B) TYPE: amino acid
          (C) STRANDEDNESS: Not Relevant
          (D) TOPOLOGY: unknown (ii) MOLECULE TYPE: protein (ix) FEATURE:
          (A) NAME/KEY: Modified-site
          (B) LOCATION: 2
          (D) OTHER INFORMATION: /note= "The Proline at this
              position is a hydroxyproline."

(ix) FEATURE:
          (A) NAME/KEY: Modified-site
          (B) LOCATION: 6
          (D) OTHER INFORMATION: /note= "The Proline at this
              position is a hydroxyproline."

(ix) FEATURE:
          (A) NAME/KEY: Modified-site
          (B) LOCATION: 8..9
          (D) OTHER INFORMATION: /note= "The Proline at these
              positions is a hydroxyproline."

(xi) SEQUENCE DESCRIPTION: SEQ ID NO:22:

Ser Pro Leu Pro Thr Pro Thr Pro Pro Leu Gly Pro His
 1               5                  10

(2) INFORMATION FOR SEQ ID NO:23:

(i) SEQUENCE CHARACTERISTICS:
          (A) LENGTH: 13 amino acids
          (B) TYPE: amino acid
          (C) STRANDEDNESS: Not Relevant
          (D) TOPOLOGY: unknown (ii) MOLECULE TYPE: protein (ix) FEATURE:
          (A) NAME/KEY: Modified-site
          (B) LOCATION: 2
          (D) OTHER INFORMATION: /note= "The Proline at this
              position is a hydroxyproline."

(ix) FEATURE:
          (A) NAME/KEY: Modified-site
          (B) LOCATION: 4
          (D) OTHER INFORMATION: /note= "The Proline at this
              position is a hydroxyproline."

(ix) FEATURE:
          (A) NAME/KEY: Modified-site
          (B) LOCATION: 6
          (D) OTHER INFORMATION: /note= "The Proline at this
              position is a hydroxyproline."

(ix) FEATURE:
          (A) NAME/KEY: Modified-site
          (B) LOCATION: 8..9
          (D) OTHER INFORMATION: /note= "The Proline at these
              positions is a hydroxyproline."

(xi) SEQUENCE DESCRIPTION: SEQ ID NO:23:
```

```
Ser Pro Ser Pro Thr Pro Thr Pro Pro Leu Gly Pro His
1               5                   10
```

(2) INFORMATION FOR SEQ ID NO:24:

(i) SEQUENCE CHARACTERISTICS:
        (A) LENGTH: 13 amino acids
        (B) TYPE: amino acid
        (C) STRANDEDNESS: Not Relevant
        (D) TOPOLOGY: unknown (ii) MOLECULE TYPE: protein (ix) FEATURE:
        (A) NAME/KEY: Modified-site
        (B) LOCATION: 2..3
        (D) OTHER INFORMATION: /note= "The Proline a these
            positions is a hydroxyproline."

(ix) FEATURE:
        (A) NAME/KEY: Modified-site
        (B) LOCATION: 6
        (D) OTHER INFORMATION: /note= "The Proline at this
            position is a hydroxyproline."

(ix) FEATURE:
        (A) NAME/KEY: Modified-site
        (B) LOCATION: 8..9
        (D) OTHER INFORMATION: /note= "The Proline at these
            positions is a hydroxyproline."

(xi) SEQUENCE DESCRIPTION: SEQ ID NO:24:

```
Ser Pro Pro Leu Thr Pro Thr Pro Pro Leu Leu Pro His
1               5                   10
```

(2) INFORMATION FOR SEQ ID NO:25:

(i) SEQUENCE CHARACTERISTICS:
        (A) LENGTH: 19 amino acids
        (B) TYPE: amino acid
        (C) STRANDEDNESS: Not Relevant
        (D) TOPOLOGY: unknown (ii) MOLECULE TYPE: protein (ix) FEATURE:
        (A) NAME/KEY: Modified-site
        (B) LOCATION: 2
        (D) OTHER INFORMATION: /note= "The Proline at this
            position is a hydroxyproline."

(ix) FEATURE:
        (A) NAME/KEY: Modified-site
        (B) LOCATION: 8
        (D) OTHER INFORMATION: /note= "The Proline at this
            position is a hydroxyproline."

(ix) FEATURE:
        (A) NAME/KEY: Modified-site
        (B) LOCATION: 12
        (D) OTHER INFORMATION: /note= "The Proline at this
            position is a hydroxyproline."

(ix) FEATURE:
        (A) NAME/KEY: Modified-site
        (B) LOCATION: 14..16
        (D) OTHER INFORMATION: /note= "The Proline at these
            positions is a hydroxyproline."

(xi) SEQUENCE DESCRIPTION: SEQ ID NO:25:

```
Ser Pro Leu Pro Thr Leu Ser Pro Leu Pro Ala Pro Thr Pro Pro Pro
1               5                   10                  15
Gly Pro His
```

(2) INFORMATION FOR SEQ ID NO:26:

(i) SEQUENCE CHARACTERISTICS:
        (A) LENGTH: 19 amino acids
        (B) TYPE: amino acid
        (C) STRANDEDNESS: Not Relevant
        (D) TOPOLOGY: unknown (ii) MOLECULE TYPE: protein (ix) FEATURE:
        (A) NAME/KEY: Modified-site
        (B) LOCATION: 2
        (D) OTHER INFORMATION: /note= "The Proline at this
            position is a hydroxyproline."

(ix) FEATURE:
        (A) NAME/KEY: Modified-site
        (B) LOCATION: 8
        (D) OTHER INFORMATION: /note= "The Proline at this
            position is a hydroxyproline."

(ix) FEATURE:
        (A) NAME/KEY: Modified-site
        (B) LOCATION: 12
        (D) OTHER INFORMATION: /note= "The Proline at this
            position is a hydroxyproline."

(ix) FEATURE:
        (A) NAME/KEY: Modified-site
        (B) LOCATION: 14..16
        (D) OTHER INFORMATION: /note= "The Proline at these
            positions is a hydroxyproline."

(xi) SEQUENCE DESCRIPTION: SEQ ID NO:26:

```
Ser Pro Leu Pro Thr Leu Ser Pro Leu Pro Thr Pro Thr Pro Pro Pro
1               5                   10                  15

Gly Pro His
```

(2) INFORMATION FOR SEQ ID NO:27:

(i) SEQUENCE CHARACTERISTICS:
        (A) LENGTH: 19 amino acids
        (B) TYPE: amino acid
        (C) STRANDEDNESS: Not Relevant
        (D) TOPOLOGY: unknown (ii) MOLECULE TYPE: protein (ix) FEATURE:
        (A) NAME/KEY: Modified-site
        (B) LOCATION: 2..4
        (D) OTHER INFORMATION: /note= "The Proline at these
            positions is a hydroxyproline."

(ix) FEATURE:
        (A) NAME/KEY: Modified-site
        (B) LOCATION: 8
        (D) OTHER INFORMATION: /note= "The Proline at this
            position is a hydroxyproline."

(ix) FEATURE:
        (A) NAME/KEY: Modified-site
        (B) LOCATION: 10
        (D) OTHER INFORMATION: /note= "The Proline at this
            position is a hydroxyproline."

(ix) FEATURE:
        (A) NAME/KEY: Modified-site
        (B) LOCATION: 12
        (D) OTHER INFORMATION: /note= "The Proline at this
            position is a hydroxyproline."

(ix) FEATURE:

```
            (A) NAME/KEY: Modified-site
            (B) LOCATION: 14..15
            (D) OTHER INFORMATION: /note= "The Proline at these
                positions is a hydroxyproline."

(xi) SEQUENCE DESCRIPTION: SEQ ID NO:27:

Ser Pro Pro Pro Thr Leu Ser Pro Ser Pro Thr Pro Thr Pro Leu
1               5                   10                  15

Gly Pro His (2) INFORMATION FOR SEQ ID NO:28:

(i) SEQUENCE CHARACTERISTICS:
            (A) LENGTH: 19 amino acids
            (B) TYPE: amino acid
            (C) STRANDEDNESS: Not Relevant
            (D) TOPOLOGY: unknown (ii) MOLECULE TYPE: protein (ix) FEATURE:
            (A) NAME/KEY: Modified-site
            (B) LOCATION: 2..5
            (D) OTHER INFORMATION: /note= "The Proline at these
                positions is a hydroxyproline."

(ix) FEATURE:
            (A) NAME/KEY: Modified-site
            (B) LOCATION: 8
            (D) OTHER INFORMATION: /note= "The Proline at this
                position is a hydroxyproline."

(ix) FEATURE:
            (A) NAME/KEY: Modified-site
            (B) LOCATION: 10
            (D) OTHER INFORMATION: /note= "The Proline at this
                position is a hydroxyproline."

(ix) FEATURE:
            (A) NAME/KEY: Modified-site
            (B) LOCATION: 12
            (D) OTHER INFORMATION: /note= "The Proline at this
                position is a hydroxyproline."

(ix) FEATURE:
            (A) NAME/KEY: Modified-site
            (B) LOCATION: 14..15
            (D) OTHER INFORMATION: /note= "The Proline at these
                positions is a hydroxyproline."

(xi) SEQUENCE DESCRIPTION: SEQ ID NO:28:

Ser Pro Pro Pro Pro Leu Ser Pro Ser Pro Thr Pro Thr Pro Leu
1               5                   10                  15

Gly Pro His (2) INFORMATION FOR SEQ ID NO:29:

(i) SEQUENCE CHARACTERISTICS:
            (A) LENGTH: 12 amino acids
            (B) TYPE: amino acid
            (C) STRANDEDNESS: Not Relevant
            (D) TOPOLOGY: unknown (ii) MOLECULE TYPE: protein (xi) SEQUENCE DESCRIPTION: SEQ ID NO:29:

Ala Gly Ser Ser Thr Arg Ala Ser Pro Pro Pro Pro
1               5                   10

(2) INFORMATION FOR SEQ ID NO:30:
```

(i) SEQUENCE CHARACTERISTICS:
        (A) LENGTH: 27 base pairs
        (B) TYPE: nucleic acid
        (C) STRANDEDNESS: both
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:30:

GCTGGATCCT CAACCCGGGC CTCACCA                                27

(2) INFORMATION FOR SEQ ID NO:31:

(i) SEQUENCE CHARACTERISTICS:
        (A) LENGTH: 36 base pairs
        (B) TYPE: nucleic acid
        (C) STRANDEDNESS: both
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:31:

AGGTGGTGGT GGTGAGCCCC GGGTTGAGGA TCCAGC                      36

(2) INFORMATION FOR SEQ ID NO:32:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:32:

Pro Pro Pro Ser Pro Val Ala Arg Asn Ser Pro Pro
1               5                   10

(2) INFORMATION FOR SEQ ID NO:33:

(i) SEQUENCE CHARACTERISTICS:
        (A) LENGTH: 36 base pairs
        (B) TYPE: nucleic acid
        (C) STRANDEDNESS: both
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:33:

CCACCACCTT CACCGGTCGC CCGGAATTCA CCACCC                      36

(2) INFORMATION FOR SEQ ID NO:34:

(i) SEQUENCE CHARACTERISTICS:
        (A) LENGTH: 27 base pairs
        (B) TYPE: nucleic acid
        (C) STRANDEDNESS: both
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:34:

GGGTGGTGAA TTCCGGGCGA CCGGTGA                                27

(2) INFORMATION FOR SEQ ID NO:35:

```
    (i) SEQUENCE CHARACTERISTICS:
         (A) LENGTH: 24 base pairs
         (B) TYPE: nucleic acid
         (C) STRANDEDNESS: both
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:35:

CCACCACCTT AATAGAGCTC CCCC                                              24

(2) INFORMATION FOR SEQ ID NO:36:

(i) SEQUENCE CHARACTERISTICS:
         (A) LENGTH: 15 base pairs
         (B) TYPE: nucleic acid
         (C) STRANDEDNESS: both
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:36:

GGGGGAGCTC TATTA                                                        15

(2) INFORMATION FOR SEQ ID NO:37:

(i) SEQUENCE CHARACTERISTICS:
         (A) LENGTH: 10 amino acids
         (B) TYPE: amino acid
         (C) STRANDEDNESS: Not Relevant
         (D) TOPOLOGY: unknown (ii) MOLECULE TYPE: protein (xi) SEQUENCE DESCRIPTION: SEQ ID NO:37:

Pro Pro Pro Ser Pro Pro Pro Pro Ser Pro
1               5                   10

(2) INFORMATION FOR SEQ ID NO:38:

(i) SEQUENCE CHARACTERISTICS:
         (A) LENGTH: 30 base pairs
         (B) TYPE: nucleic acid
         (C) STRANDEDNESS: both
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:38:

CCACCACCTT CACCTCCACC CCCATCTCCA                                        30

(2) INFORMATION FOR SEQ ID NO:39:

(i) SEQUENCE CHARACTERISTICS:
         (A) LENGTH: 30 base pairs
         (B) TYPE: nucleic acid
         (C) STRANDEDNESS: both
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:39:

AGGTGGTGGT GGAGATGGGG GTGGAGGTGA                                        30
```

(2) INFORMATION FOR SEQ ID NO:40:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:40:

```
Ala Ala Gly Ser Ser Thr Arg Ala Ser Pro Ser
1               5                   10
```

(2) INFORMATION FOR SEQ ID NO:41:

(i) SEQUENCE CHARACTERISTICS:
        (A) LENGTH: 24 base pairs
        (B) TYPE: nucleic acid
        (C) STRANDEDNESS: both
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:41:

GCTGCCGGAT CCTCAACCCG GGCC                                      24

(2) INFORMATION FOR SEQ ID NO:42:

(i) SEQUENCE CHARACTERISTICS:
        (A) LENGTH: 33 base pairs
        (B) TYPE: nucleic acid
        (C) STRANDEDNESS: both
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:42:

TGACGGTGAG GCCCGGGTTG AGGATCCGGC AGC                         33

(2) INFORMATION FOR SEQ ID NO:43:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:43:

```
Ser Pro Ser Pro Val Ala Arg Asn Ser Pro Pro
1               5                   10
```

(2) INFORMATION FOR SEQ ID NO:44:

(i) SEQUENCE CHARACTERISTICS:
        (A) LENGTH: 33 base pairs
        (B) TYPE: nucleic acid
        (C) STRANDEDNESS: both
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:44:

TCACCCTCAC CGGTCGCCCG GAATTCACCA CCC                         33

(2) INFORMATION FOR SEQ ID NO:45:

(i) SEQUENCE CHARACTERISTICS:
        (A) LENGTH: 24 base pairs
        (B) TYPE: nucleic acid
        (C) STRANDEDNESS: both
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:45:

GGGTGGTGAA TTCCGGGCGA CCGG                                              24

(2) INFORMATION FOR SEQ ID NO:46:

(i) SEQUENCE CHARACTERISTICS:
        (A) LENGTH: 24 base pairs
        (B) TYPE: nucleic acid
        (C) STRANDEDNESS: both
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:46:

TCACCCTCAT AATAGAGCTC CCCC                                              24

(2) INFORMATION FOR SEQ ID NO:47:

(i) SEQUENCE CHARACTERISTICS:
        (A) LENGTH: 15 base pairs
        (B) TYPE: nucleic acid
        (C) STRANDEDNESS: both
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:47:

GGGGGAGCTC TATTA                                                              15

(2) INFORMATION FOR SEQ ID NO:48:

(i) SEQUENCE CHARACTERISTICS:
        (A) LENGTH: 19 amino acids
        (B) TYPE: amino acid
        (C) STRANDEDNESS: Not Relevant
        (D) TOPOLOGY: unknown (ii) MOLECULE TYPE: protein (xi) SEQUENCE DESCRIPTION: SEQ ID NO:48:

Ser Pro Ser Pro Thr Pro Thr Pro Pro Pro Gly Pro His Ser Pro Pro
1                5                     10                 15

Pro Thr Leu (2) INFORMATION FOR SEQ ID NO:49:

(i) SEQUENCE CHARACTERISTICS:
        (A) LENGTH: 57 base pairs
        (B) TYPE: nucleic acid
        (C) STRANDEDNESS: both
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:49:

```
TCACCCTCAC CAACTCCTAC CCCACCACCT GGTCCACACT CACCACCACC AACATTG        57
```

(2) INFORMATION FOR SEQ ID NO:50:

(i) SEQUENCE CHARACTERISTICS:
        (A) LENGTH: 57 base pairs
        (B) TYPE: nucleic acid
        (C) STRANDEDNESS: both
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:50:

```
TGAGGGTGAC AATGTTGGTG GTGGTGAGTG TGGACCAGGT GGTGGGGTAG GAGTTGG        57
```

(2) INFORMATION FOR SEQ ID NO:51:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: unknown (ii) MOLECULE TYPE: protein (ix) FEATURE:
        (A) NAME/KEY: Modified-site
        (B) LOCATION: 8
        (D) OTHER INFORMATION: /note= "The Proline at this
            position is a hydroxyproline."

(xi) SEQUENCE DESCRIPTION: SEQ ID NO:51:

```
Val Lys Pro Tyr His Pro Thr Pro Val Tyr Lys
1               5                   10
```

(2) INFORMATION FOR SEQ ID NO:52:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:52:

```
TCACCCTCAC CATCTCCTTC GCCATCACCC                                      30
```

(2) INFORMATION FOR SEQ ID NO:53:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:53:

```
TGAGGGTGAG GGTGATGGCG AAGGAGATGG                                      30
```

(2) INFORMATION FOR SEQ ID NO:54:

(i) SEQUENCE CHARACTERISTICS:
        (A) LENGTH: 30 base pairs
        (B) TYPE: nucleic acid (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:54:

GCTCCAGCAC CTGCCCCAGC CCCTGCACCA                                              30

(2) INFORMATION FOR SEQ ID NO:55:

(i) SEQUENCE CHARACTERISTICS:
        (A) LENGTH: 21 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:55:

TGGTGCAGGG GCTGGGGCAG G                                                       21

(2) INFORMATION FOR SEQ ID NO:56:

(i) SEQUENCE CHARACTERISTICS:
        (A) LENGTH: 21 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:56:

GCTGCCGGAT CCTCAACCCG G                                                       21

(2) INFORMATION FOR SEQ ID NO:57:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:57:

TGCTGGAGCC CGGGTTGAGG ATCCGGCAGC                                              30

(2) INFORMATION FOR SEQ ID NO:58:

(i) SEQUENCE CHARACTERISTICS:
        (A) LENGTH: 33 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:58:

GCTCCAGCAC CGGTCGCCCG GAATTCACCA CCC                                          33

(2) INFORMATION FOR SEQ ID NO:59:

(i) SEQUENCE CHARACTERISTICS:
        (A) LENGTH: 24 base pairs (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:59:

GGGTGGTGAA TTCCGGGCGA CCGG                                              24

(2) INFORMATION FOR SEQ ID NO:60:

(i) SEQUENCE CHARACTERISTICS:
        (A) LENGTH: 24 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:60:

GCTCCAGCAT AATAGAGCTC CCCC                                              24

(2) INFORMATION FOR SEQ ID NO:61:

(i) SEQUENCE CHARACTERISTICS:
        (A) LENGTH: 15 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:61:

GGGGGAGCTC TATTA                                                        15

(2) INFORMATION FOR SEQ ID NO:62:

(i) SEQUENCE CHARACTERISTICS:
        (A) LENGTH: 42 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:62:

ACACCAACCC CTACTCCCAC GCCAACACCT ACACCCACTC CA                          42

(2) INFORMATION FOR SEQ ID NO:63:

(i) SEQUENCE CHARACTERISTICS:
        (A) LENGTH: 42 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:63:

GGTTGGTGTT GGAGTGGGTC TAGGTGTTGG CGTGGGAGTA GG                          42

(2) INFORMATION FOR SEQ ID NO:64:

(i) SEQUENCE CHARACTERISTICS:

```
        (A) LENGTH: 21 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:64:

GCTGCCGGAT CCTCAACCCG G                                              21

(2) INFORMATION FOR SEQ ID NO:65:

(i) SEQUENCE CHARACTERISTICS:
        (A) LENGTH: 30 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:65:

GGTTGGTGTC CGGGTTGAGG ATCCGGCAGC                                     30

(2) INFORMATION FOR SEQ ID NO:66:

(i) SEQUENCE CHARACTERISTICS:
        (A) LENGTH: 33 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:66:

ACACCAACCC CGGTCGCCCG GAATTCACCA CCC                                 33

(2) INFORMATION FOR SEQ ID NO:67:

(i) SEQUENCE CHARACTERISTICS:
        (A) LENGTH: 24 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:67:

GGGTGGTGAA TTCCGGGCGA CCGG                                           24

(2) INFORMATION FOR SEQ ID NO:68:

(i) SEQUENCE CHARACTERISTICS:
        (A) LENGTH: 24 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:68:

ACACCAACCT AATAGAGCTC CCCC                                           24

(2) INFORMATION FOR SEQ ID NO:69:
```

(i) SEQUENCE CHARACTERISTICS:
       (A) LENGTH: 15 base pairs
       (B) TYPE: nucleic acid
       (C) STRANDEDNESS: single
       (D) TOPOLOGY: unknown (ii) MOLECULE TYPE: other nucleic acid
       (A) DESCRIPTION: /desc = "DNA"

(xi) SEQUENCE DESCRIPTION: SEQ ID NO:69:

GGGGGAGCTC TATTA                                                15

(2) INFORMATION FOR SEQ ID NO:70:

(i) SEQUENCE CHARACTERISTICS:
       (A) LENGTH: 45 base pairs
       (B) TYPE: nucleic acid
       (C) STRANDEDNESS: single
       (D) TOPOLOGY: unknown (ii) MOLECULE TYPE: other nucleic acid
       (A) DESCRIPTION: /desc = "DNA"

(xi) SEQUENCE DESCRIPTION: SEQ ID NO:70:

CCACCATCAC CACCCTCTCC TCCATCACCC CCATCCCCAC CATCA               45

(2) INFORMATION FOR SEQ ID NO:71:

(i) SEQUENCE CHARACTERISTICS:
       (A) LENGTH: 45 base pairs
       (B) TYPE: nucleic acid
       (C) STRANDEDNESS: single
       (D) TOPOLOGY: unknown (ii) MOLECULE TYPE: other nucleic acid
       (A) DESCRIPTION: /desc = "DNA"

(xi) SEQUENCE DESCRIPTION: SEQ ID NO:71:

TGATGGTGGT GATGGTGGGG ATGGGGGTGA TGGAGGAGAG GGTGG               45

(2) INFORMATION FOR SEQ ID NO:72:

(i) SEQUENCE CHARACTERISTICS:
       (A) LENGTH: 24 base pairs
       (B) TYPE: nucleic acid
       (C) STRANDEDNESS: single
       (D) TOPOLOGY: unknown (ii) MOLECULE TYPE: other nucleic acid
       (A) DESCRIPTION: /desc = "DNA"

(xi) SEQUENCE DESCRIPTION: SEQ ID NO:72:

GCTGCCGGAT CCTCAACCCG GGCC                                      24

(2) INFORMATION FOR SEQ ID NO:73:

(i) SEQUENCE CHARACTERISTICS:
       (A) LENGTH: 33 base pairs
       (B) TYPE: nucleic acid
       (C) STRANDEDNESS: single
       (D) TOPOLOGY: unknown (ii) MOLECULE TYPE: other nucleic acid
       (A) DESCRIPTION: /desc = "DNA"

(xi) SEQUENCE DESCRIPTION: SEQ ID NO:73:

TGATGGTGGG GCCCGGGTTG AGGATCCGGC AGC                            33

(2) INFORMATION FOR SEQ ID NO:74:

(i) SEQUENCE CHARACTERISTICS:
    (A) LENGTH: 33 base pairs
    (B) TYPE: nucleic acid
    (C) STRANDEDNESS: single
    (D) TOPOLOGY: unknown (ii) MOLECULE TYPE: other nucleic acid
    (A) DESCRIPTION: /desc = "DNA"

(xi) SEQUENCE DESCRIPTION: SEQ ID NO:74:

CCACCATCAC CGGTCGCCCG GAATTCACCA CCC                              33

(2) INFORMATION FOR SEQ ID NO:75:

(i) SEQUENCE CHARACTERISTICS:
        (A) LENGTH: 24 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:75:

GGGTGGTGAA TTCCGGGCGA CCGG                                       24

(2) INFORMATION FOR SEQ ID NO:76:

(i) SEQUENCE CHARACTERISTICS:
        (A) LENGTH: 24 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:76:

CCACCATCAT AATAGAGCTC CCCC                                       24

(2) INFORMATION FOR SEQ ID NO:77:

(i) SEQUENCE CHARACTERISTICS:
        (A) LENGTH: 15 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:77:

GGGGGAGCTC TATTA                                                 15

(2) INFORMATION FOR SEQ ID NO:78:

(i) SEQUENCE CHARACTERISTICS:
        (A) LENGTH: 48 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:78:

CCACCACCTT CACCACCTCC ATCTCCCCCA CCTTCCCCTC CACCATCA             48

(2) INFORMATION FOR SEQ ID NO:79:

(i) SEQUENCE CHARACTERISTICS:
        (A) LENGTH: 48 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:79:

```
AGGTGGTGGT GATGGTGGAG GGGAAGGTGG GGGAGATGGA GGTGGTGA                    48
```

(2) INFORMATION FOR SEQ ID NO:80:

(i) SEQUENCE CHARACTERISTICS:
        (A) LENGTH: 24 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:80:

```
GCTGGATCCT CAACCCGGGC CTCA                                              24
```

(2) INFORMATION FOR SEQ ID NO:81:

(i) SEQUENCE CHARACTERISTICS:
        (A) LENGTH: 33 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:81:

```
AGGTGGTGGT GAGGCCCGGG TTGAGGATCC AGC                                    33
```

(2) INFORMATION FOR SEQ ID NO:82:

(i) SEQUENCE CHARACTERISTICS:
        (A) LENGTH: 36 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:82:

```
CCACCACCTT CACCGGTCGC CCGGAATTCA CCACCC                                 36
```

(2) INFORMATION FOR SEQ ID NO:83:

(i) SEQUENCE CHARACTERISTICS:
        (A) LENGTH: 27 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:83:

```
GGGTGGTGAA TTCCGGGCGA CCGGTGA                                           27
```

(2) INFORMATION FOR SEQ ID NO:84:

(i) SEQUENCE CHARACTERISTICS:
        (A) LENGTH: 24 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:84:

CCACCACCTT AATAGAGCTC CCCC                        24

(2) INFORMATION FOR SEQ ID NO:85:

(i) SEQUENCE CHARACTERISTICS:
        (A) LENGTH: 15 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:85:

GGGGGAGCTC TATTA                               15

(2) INFORMATION FOR SEQ ID NO:86:

(i) SEQUENCE CHARACTERISTICS:
        (A) LENGTH: 42 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:86:

CCACCACCTT CACCCTCTCC ACCTCCACCA TCTCCGTCAC CA          42

(2) INFORMATION FOR SEQ ID NO:87:

(i) SEQUENCE CHARACTERISTICS:
        (A) LENGTH: 42 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:87:

AGGTGGTGGT GGTGACGGAG ATGGTGGAGG TGGAGAGGGT GA          42

(2) INFORMATION FOR SEQ ID NO:88:

(i) SEQUENCE CHARACTERISTICS:
        (A) LENGTH: 48 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:88:

CCACCACCTT CACCCCCATC TCCACCTCCA CCATCTCCAC CGTCACCA      48

(2) INFORMATION FOR SEQ ID NO:89:

(i) SEQUENCE CHARACTERISTICS:
        (A) LENGTH: 48 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:89:

```
AGGTGGTGGT GGTGACGGTG GAGATGGTGG AGGTGGAGAT GGGGGTGA            48
```

(2) INFORMATION FOR SEQ ID NO:90:

(i) SEQUENCE CHARACTERISTICS:
        (A) LENGTH: 60 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:90:

```
CCACCACCTA CTCCCGTTTA CAAATCACCA CCACCACCTA CTCCCGTTTA CAAATCACCA    60
```

(2) INFORMATION FOR SEQ ID NO:91:

(i) SEQUENCE CHARACTERISTICS:
        (A) LENGTH: 60 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:91:

```
AGGTGGTGGT GGTGATTTGT AAACGGGAGT AGGTGGTGGT GGTGATTTGT AAACGGGAGT    60
```

(2) INFORMATION FOR SEQ ID NO:92:

(i) SEQUENCE CHARACTERISTICS:
        (A) LENGTH: 48 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:92:

```
CCACCACCTG TCAAGCCTTA CCACCCCACT CCCGTTTTTC TTTCACCA            48
```

(2) INFORMATION FOR SEQ ID NO:93:

(i) SEQUENCE CHARACTERISTICS:
        (A) LENGTH: 48 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:93:

AGGTGGTGGT GGTGAAAGAA AACGGGAGT GGGGTGGTAA GGCTTGAC                48

(2) INFORMATION FOR SEQ ID NO:94:

(i) SEQUENCE CHARACTERISTICS:
        (A) LENGTH: 48 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:94:

CCACCACCTG TCTTACCTTT CCACCCCACT CCCGTTTACA AATCACCA              48

(2) INFORMATION FOR SEQ ID NO:95:

(i) SEQUENCE CHARACTERISTICS:
        (A) LENGTH: 48 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:95:

AGGTGGTGGT GGTGATTTGT AAACGGGAGT GGGGTGGAAA GGTAAGAC              48

(2) INFORMATION FOR SEQ ID NO:96:

(i) SEQUENCE CHARACTERISTICS:
        (A) LENGTH: 21 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:96:

GGCCGCGAGC TCCAGCACGG G                                          21

(2) INFORMATION FOR SEQ ID NO:97:

(i) SEQUENCE CHARACTERISTICS:
        (A) LENGTH: 17 base pairs
        (B) TYPE: nucleic acid
        (C) STRANDEDNESS: single
        (D) TOPOLOGY: unknown (ii) MOLECULE TYPE: other nucleic acid
        (A) DESCRIPTION: /desc = "DNA"

(xi) SEQUENCE DESCRIPTION: SEQ ID NO:97:

CCCGTGCTGG AGCTCGC                                               17

(2) INFORMATION FOR SEQ ID NO:98:

(i) SEQUENCE CHARACTERISTICS:
        (A) LENGTH: 121 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:98:

```
GATCCGCAAT GGGAAAAATG GCTTCTCTAT TTGCCACATT TTTAGTGGTT TTAGTGTCAC      60

TTAGCTTAGC ACAAACAACC CGGGTACCGG TCGCCACCAT GGTGTAAAGC GGCCGCGAGC     120

T                                                                     121
```

(2) INFORMATION FOR SEQ ID NO:99:

(i) SEQUENCE CHARACTERISTICS:
        (A) LENGTH: 113 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:99:

```
CGCGGCCGCT TTACACCATG GTGGCGACCG GTACCCGGGT TGTTTGTGCT AAGCTAAGTG      60

ACACTAAAAC CACTAAAAAT GTGGCAAATA GAGAAGCCAT TTTTCCCATT GCG            113
```

(2) INFORMATION FOR SEQ ID NO:100:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: unknown (ii) MOLECULE TYPE: protein (ix) FEATURE:
        (A) NAME/KEY: Modified-site
        (B) LOCATION: 2..4
        (D) OTHER INFORMATION: /note= "The proline at positions 2,
            3, and 4 is a hydroxyproline."

(ix) FEATURE:
        (A) NAME/KEY: Modified-site
        (B) LOCATION: 5
        (D) OTHER INFORMATION: /note= "Xaa is a hydroxyproline or
            Threonine."

(xi) SEQUENCE DESCRIPTION: SEQ ID NO:100:

```
Ser Pro Pro Pro Xaa
1               5
```

(2) INFORMATION FOR SEQ ID NO:101:

(i) SEQUENCE CHARACTERISTICS:
        (A) LENGTH: 4 amino acids
        (B) TYPE: amino acid
        (C) STRANDEDNESS: Not Relevant
        (D) TOPOLOGY: unknown (ii) MOLECULE TYPE: protein (ix) FEATURE:
        (A) NAME/KEY: Modified-site
        (B) LOCATION: 1
        (D) OTHER INFORMATION: /note= "Xaa is an amino acid other
            than hydroxyproline."

(ix) FEATURE:
        (A) NAME/KEY: Modified-site
        (B) LOCATION: 2
        (D) OTHER INFORMATION: /note= "The Proline at this
            position is a hydroxyproline."

(ix) FEATURE:
        (A) NAME/KEY: Modified-site
        (B) LOCATION: 3

(D) OTHER INFORMATION: /note= "Xaa is an amino acid other
            than hydroxyproline."

(ix) FEATURE:
        (A) NAME/KEY: Modified-site
        (B) LOCATION: 4
        (D) OTHER INFORMATION: /note= "The Proline at this
            position is a hydroxyproline."

(xi) SEQUENCE DESCRIPTION: SEQ ID NO:101:

Xaa Pro Xaa Pro
    1

(2) INFORMATION FOR SEQ ID NO:102:

(i) SEQUENCE CHARACTERISTICS:
        (A) LENGTH: 4 amino acids
        (B) TYPE: amino acid
        (C) STRANDEDNESS: Not Relevant
        (D) TOPOLOGY: unknown (ii) MOLECULE TYPE: protein (ix) FEATURE:
        (A) NAME/KEY: Modified-site
        (B) LOCATION: 2
        (D) OTHER INFORMATION: /note= "The proline at this
            position is a hydroxyproline."

(ix) FEATURE:
        (A) NAME/KEY: Modified-site
        (B) LOCATION: 4
        (D) OTHER INFORMATION: /note= "The proline at this
            position is a hydroxyproline."

(xi) SEQUENCE DESCRIPTION: SEQ ID NO:102:

Ser Pro Ser Pro
1

(2) INFORMATION FOR SEQ ID NO:103:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: unknown (ii) MOLECULE TYPE: protein (ix) FEATURE:
        (A) NAME/KEY: Modified-site
        (B) LOCATION: 2
        (D) OTHER INFORMATION: /note= "The proline at this
            position is a hydroxyproline."

(ix) FEATURE:
        (A) NAME/KEY: Modified-site
        (B) LOCATION: 4..6
        (D) OTHER INFORMATION: /note= "The proline at positions 4,
            5, and 6 is a hydroxyproline."

(xi) SEQUENCE DESCRIPTION: SEQ ID NO:103:

Thr Pro Thr Pro Pro Pro
1               5

(2) INFORMATION FOR SEQ ID NO:104:

(i) SEQUENCE CHARACTERISTICS:
        (A) LENGTH: 19 amino acids
        (B) TYPE: amino acid
        (C) STRANDEDNESS: Not Relevant
        (D) TOPOLOGY: unknown

```
    (ii) MOLECULE TYPE: protein (ix) FEATURE:
         (A) NAME/KEY: Modified-site
         (B) LOCATION: 1
         (D) OTHER INFORMATION: /note= "Xaa is Leu or nothing."

(ix) FEATURE:
         (A) NAME/KEY: Modified-site
         (B) LOCATION: 2..4
         (D) OTHER INFORMATION: /note= "The proline at positions 2,
             3, and 4 is a hydroxyproline."

(ix) FEATURE:
         (A) NAME/KEY: Modified-site
         (B) LOCATION: 5..6
         (D) OTHER INFORMATION: /note= "Xaa at positions 5 and 6 is
             Leu or nothing."

(ix) FEATURE:
         (A) NAME/KEY: Modified-site
         (B) LOCATION: 8
         (D) OTHER INFORMATION: /note= "The proline at this
             position is a hydroxyproline."

(ix) FEATURE:
         (A) NAME/KEY: Modified-site
         (B) LOCATION: 10
         (D) OTHER INFORMATION: /note= "The proline at this
             position is a hydroxyproline."

(ix) FEATURE:
         (A) NAME/KEY: Modified-site
         (B) LOCATION: 12
         (D) OTHER INFORMATION: /note= "The proline at this
             position is a hydroxyproline."

(ix) FEATURE:
         (A) NAME/KEY: Modified-site
         (B) LOCATION: 14..16
         (D) OTHER INFORMATION: /note= "The proline at positions
             14, 15, and 16 is a hydroxyproline."

(ix) FEATURE:
         (A) NAME/KEY: Modified-site
         (B) LOCATION: 17
         (D) OTHER INFORMATION: /note= "Xaa at position 17 is Leu
             or nothing."

(ix) FEATURE:
         (A) NAME/KEY: Modified-site
         (B) LOCATION: 18
         (D) OTHER INFORMATION: /note= "Xaa at position 18 is Pro
             or nothing."

(ix) FEATURE:
         (A) NAME/KEY: Modified-site
         (B) LOCATION: 19
         (D) OTHER INFORMATION: /note= "Xaa at position 19 is His
             or nothing."

(xi) SEQUENCE DESCRIPTION: SEQ ID NO:104:

Xaa Pro Pro Pro Xaa Xaa Ser Pro Ser Pro Thr Pro Thr Pro Pro Pro
1               5                   10                  15

Xaa Xaa Xaa (2) INFORMATION FOR SEQ ID NO:105:

(i) SEQUENCE CHARACTERISTICS:
         (A) LENGTH: 5 amino acids
         (B) TYPE: amino acid
         (C) STRANDEDNESS: Not Relevant
         (D) TOPOLOGY: unknown (ii) MOLECULE TYPE: protein
```

-continued

```
    (ix) FEATURE:
         (A) NAME/KEY: Modified-site
         (B) LOCATION: 2..5
         (D) OTHER INFORMATION: /note= "The proline at positions 2,
             3, 4, and 5 is a hydroxyproline."

(xi) SEQUENCE DESCRIPTION: SEQ ID NO:105:

Ser Pro Pro Pro Pro
1               5

(2) INFORMATION FOR SEQ ID NO:106:

(i) SEQUENCE CHARACTERISTICS:
         (A) LENGTH: 5 amino acids
         (B) TYPE: amino acid
         (C) STRANDEDNESS: Not Relevant
         (D) TOPOLOGY: unknown (ii) MOLECULE TYPE: protein (ix) FEATURE:
         (A) NAME/KEY: Modified-site
         (B) LOCATION: 2..4
         (D) OTHER INFORMATION: /note= "The proline at positions 2,
             3, and 4 is a hydroxyproline."

(xi) SEQUENCE DESCRIPTION: SEQ ID NO:106:

Ser Pro Pro Pro Thr
1               5
```